US012766489B2

(12) United States Patent
Zhang et al.

(10) Patent No.: US 12,766,489 B2
(45) Date of Patent: Oct. 20, 2026

(54) METHOD FOR SYNTHESIZING AMORPHOUS Pd-BASED NANOPARTICLES

(71) Applicant: City University of Hong Kong, Hong Kong (HK)

(72) Inventors: Hua Zhang, Hong Kong (HK); Yiyao Ge, Hong Kong (HK)

(73) Assignee: City University of Hong Kong, Hong Kong (HK)

( * ) Notice: Subject to any disclaimer, the term of this patent is extended or adjusted under 35 U.S.C. 154(b) by 650 days.

(21) Appl. No.: 18/181,593

(22) Filed: Mar. 10, 2023

(65) Prior Publication Data

US 2023/0338930 A1 Oct. 26, 2023

Related U.S. Application Data

(60) Provisional application No. 63/334,655, filed on Apr. 25, 2022.

(51) Int. Cl.
*B01J 23/46* (2006.01)
*B01J 21/18* (2006.01)
(Continued)

(52) U.S. Cl.
CPC ............ *B01J 23/462* (2013.01); *B01J 21/18* (2013.01); *B01J 35/45* (2024.01); *B01J 37/009* (2013.01);
(Continued)

(58) Field of Classification Search
CPC ........................................................ B22F 9/24
See application file for complete search history.

(56) References Cited

U.S. PATENT DOCUMENTS

2018/0221961 A1* 8/2018 Bakr ......................... F27D 1/00
2020/0248282 A1 8/2020 He et al.

FOREIGN PATENT DOCUMENTS

CN 1485171 A 3/2004
CN 108425080 A 8/2018

OTHER PUBLICATIONS

Zhao, Ming, et al. "Fabrication of Pd—Ni—P metallic glass nanoparticles and their application as highly durable catalysts in methanol electro-oxidation." Chemistry of Materials 26.2 (2014): 1056-1061. (Year: 2014).*

(Continued)

*Primary Examiner* — Keith D. Hendricks
*Assistant Examiner* — Joshua S Carpenter
(74) *Attorney, Agent, or Firm* — IDEA Intellectual Limited; Sam T. Yip

(57) ABSTRACT

A general and controlled method for synthesizing amorphous Pd-based nanoparticles is provided. The method comprises: dissolving Pd precursor in a first solvent to form a first solution; mixing the first solution with a second solvent to form a first mixture; adding surfactant into the first mixture to form a second mixture; heating the second mixture to render a second solution; adding metal precursor into the second solution to form a third mixture; heating the third mixture to render a third solution; naturally cooling down the third solution; adding ethanol to the third solution to form a fourth solution; and collecting the amorphous Pd-based nanoparticles from the fourth solution. The method allows tuning of phase of Pd-based nanoparticles to obtain amorphous Pd-based nanocatalysts to efficiently switch ring-opening route of epoxides for the synthesis of distinct targeted chemicals and modulating of catalytic performance thereof in hydrogen emission reactions.

18 Claims, 27 Drawing Sheets

(51) Int. Cl.

| | |
|---|---|
| ***B01J 35/45*** | (2024.01) |
| ***B01J 37/00*** | (2006.01) |
| ***B01J 37/02*** | (2006.01) |
| ***B01J 37/03*** | (2006.01) |
| ***B01J 37/04*** | (2006.01) |
| ***B01J 37/06*** | (2006.01) |
| ***B01J 37/34*** | (2006.01) |
| ***B22F 1/054*** | (2022.01) |
| ***B22F 9/24*** | (2006.01) |
| ***C07C 29/10*** | (2006.01) |

(52) U.S. Cl.

CPC ......... *B01J 37/0221* (2013.01); *B01J 37/031* (2013.01); *B01J 37/04* (2013.01); *B01J 37/06* (2013.01); *B01J 37/343* (2013.01); *B22F 1/054* (2022.01); *B22F 9/24* (2013.01); *C07C 29/106* (2013.01)

(56) References Cited

OTHER PUBLICATIONS

Wei Lu et al. Synthesis and Characterization of Crystalline and Amorphous Palladium Nanoparticles. Langmuir, 2003, 19, 5887-5891.
Yiyao Ge et al. Phase-Selective Epitaxial Growth of Heterophase Nanostructures on Unconventional 2H—Pd Nanoparticles. J. Am. Chem. Soc. 2020, 142, 18971-18980.
Gastón Corthey et al. Influence of Capping on the Atomistic Arrangement in Palladium Nanoparticles at Room Temperature. J. Phys. Chem. C, 2014, 118, 24641-24647.
Hongfei Cheng et al. Ligand-Exchange-Induced Amorphization of Pd Nanomaterials for Highly Efficient Electrocatalytic Hydrogen Evolution Reaction. Adv. Mater. 2020, 32, 1902964.
Weicong Wang et al. General Synthesis of Amorphous PdM (M = Cu, Fe, Co, Ni) Alloy Nanowires for Boosting HCOOH Dehydrogenation. Nano Lett. 2021, 21, 3458-3464.
Yifeng Shi et al. Noble-Metal Nanocrystals with Controlled Shapes for Catalytic and Electrocatalytic Applications. Chem. Rev. 2021, 121, 649-735.
Tung-Han Yang et al. Noble-Metal Nanoframes and Their Catalytic Applications. Chem. Rev. 2021, 121, 796-833.
Leigang Li et al. Metallic nanostructures with low dimensionality for electrochemical water splitting. Chem. Soc. Rev. 2020, 49, 3072-3106.
Ye Chen et al. Two-Dimensional Metal Nanomaterials: Synthesis, Properties, and Applications. Chem. Rev. 2018, 118, 6409-6455.
Lina Cao et al. Atomically dispersed iron hydroxide anchored on Pt for preferential oxidation of CO in H2. Nature, 2019, 565, 631-635.
Xinlong Tian et al. Engineering bunched Pt—Ni alloy nanocages for efficient oxygen reduction in practical fuel cells. Science, 2019, 366, 850-856.
Xiaoqing Huang et al. High-performance transition metal-doped Pt3Ni octahedra for oxygen reduction reaction. Science, 2015, 348, 1230-1234.
Cheng-Long Yang et al. Sulfur-anchoring synthesis of platinum intermetallic nanoparticle catalysts for fuel cells. Science, 2021, 374, 459-464.
Ye Chen et al. Phase engineering of nanomaterials. Nature Reviews Chemistry, 2020, 4, 243-256.
Jiawei Liu et al. Unconventional-Phase Crystalline Materials Constructed from Multiscale Building Blocks. Chem. Rev. 2021, 121, 5830-5888.
Ming Zhao et al. Crystal-phase and surface-structure engineering of ruthenium nanocrystals. Nat. Rev. Materials, 2020, 5, 440-459.
Yiyao Ge et al. Two-Dimensional Nanomaterials with Unconventional Phases. Chem 6, 2020, 1237-1253.
Xiao Zhang et al. Lithiation-induced amorphization of Pd3P2S8 for highly efficient hydrogen evolution. Nature Catalysis, 2018, 1, 460-468.
Jinzhe Liang et al. Wet-chemical synthesis and applications of amorphous metal-containing nanomaterials. Nano Res. 2021, https://doi.org/10.1007/s12274-021-4007-6.
Hewei Zhao et al. Wet Chemical Synthesis of Amorphous Nanomaterials with Well-Defined Morphologies. Acc. Mater. Res. 2021, 2, 804-815.
Jingjie Ge et al. Ultrathin Amorphous/Crystalline Heterophase Rh and Rh Alloy Nanosheets as Tandem Catalysts for Direct Indole Synthesis. Adv. Mater. 2021, 33, 2006711.
Geng Wu et al. A general synthesis approach for amorphous noble metal nanosheets. Nature Communications, 2019, 10, 4855.
Si-Jia Li et al. Amorphizing of Au Nanoparticles by Ceox-RGO Hybrid Support towards Highly Efficient Electrocatalyst for N2 Reduction under Ambient Conditions. Adv. Mater. 2017, 29, 1700001.
Mingchuan Luo et al. PdMo bimetallene for oxygen reduction catalysis. Nature, 2019, 574, 81-85.
Mingchuan Luo et al. Strain-controlled electrocatalysis on multimetallic nanomaterials. Nature Reviews Materials, 2017, 2, 17059.
Ming Zhou et al. Noble-Metal Based Random Alloy and Intermetallic Nanocrystals: Syntheses and Applications. Chem. Rev. 2021, 121, 736-795.
Kyle D. Gilroy et al. Bimetallic Nanocrystals: Syntheses, Properties, and Applications. Chem. Rev. 2016, 116, 10414-10472.
Aicheng Chen et al. Palladium-Based Nanomaterials: Synthesis and Electrochemical Applications. Chem. Rev. 2015, 115, 11999-12044.
Nailiang Yang et al. Amorphous/Crystalline Hetero-Phase Pd Nanosheets: One-Pot Synthesis and Highly Selective Hydrogenation Reaction. Adv. Mater. 2018, 30, 1803234.
Marion Duval et al. Selective palladium nanoparticles-catalyzed hydrogenolysis of industrially targeted epoxides in water. Journal Catalysis, 2021, 396, 261-268.
Xichen Zhou et al. Preparation of Au@Pd Core-Shell Nanorods with fcc-2H-fcc Heterophase for Highly Efficient Electrocatalytic Alcohol Oxidation. J. Am. Chem. Soc. 2022, 144, 547-555.
Yiyao Ge et al. Seeded Synthesis of Unconventional 2H-Phase Pd Alloy Nanomaterials for Highly Efficient Oxygen Reduction. J. Am. Chem. Soc. 2021, 143, 17292-17299.
Gastón Corthey et al. New Insights into the Chemistry of Thiolate-Protected Palladium Nanoparticles. J. Phys. Chem. C, 2012, 116, 9830-9837.
Nassira Chakroune et al. Acetate- and Thiol-Capped Monodisperse Ruthenium Nanoparticles: XPS, XAS, and HRTEM Studies. Langmuir, 2005, 21, 6788-6796.
Chengbo Yao et al. Anti-Markovnikov alcohols via epoxide hydrogenation through cooperative catalysis. Science, 2019, 364, 764-767.
Weiping Liu et al. Iron-catalysed regioselective hydrogenation of terminal epoxides to alcohols under mild conditions. Nature Catalysis, 2019, 2, 523-528.
Yu-Xiao Zhou et al. MIL-101-SO3H: A Highly Efficient Bronsted Acid Catalyst for Heterogeneous Alcoholysis of Epoxides under Ambient Conditions. Chem. Eur. J. 2014, 20, 14976-14980.
M.M. Telkar et al. Shape-controlled preparation and catalytic activity of metal nanoparticles for hydrogenation of 2-butyne-1,4-diol and styrene oxide. Applied Catalysis A: General, 2004, 273, 11-19.
Sofia M. Bruno et al. Acid-catalyzed epoxide alcoholysis in the presence of indenyl molybdenum carbonyl complexes. Journal of Organometallic Chemistry, 2018, 855, 12-17.
Leigang Li et al. Compensating Electronic Effect Enables Fast Site-to-Site Electron Transfer over Ultrathin Rumn Nanosheet Branches toward Highly Electroactive and Stable Water Splitting. Adv. Mater. 2021, 33, 2105308.
Carlos G. Morales-Guio et al. Nanostructured hydrotreating catalysts for electrochemical hydrogen evolution. Chem. Soc. Rev. 2014, 43, 6555-6569.
Qiqi Mao et al. PdRh bimetallene for energy-saving hydrogen production via methanol electroreforming. Applied Materials Today, 2022, 26, 101400.
Bożena Łosiewicz et al. Study of the hydrogen absorption/diffusion in Pd80Rh20 alloy in acidic solution. Journal of Electroanalytical Chemistry, 2018, 822, 153-162.
Yi Liu et al. Surfactant-Induced Postsynthetic Modulation of Pd Nanoparticle Crystallinity. Nano Lett. 2011, 11, 1614-1617.

(56) References Cited

OTHER PUBLICATIONS

Xiongwu Kang et al. PdRu alloy nanoparticles of solid solution in atomic scale: Size effects on electronic structure and catalytic activity towards electrooxidation of formic acid and methanol. Journal of Catalysis, 2018, 364, 183-191.
Wei Zhu et al. Evolution of surface of Pd—Rh bimetallic nanocubes and its correlation with CO oxidation. Sci. China Mater. 2019, 62(1), 103-114.
Mathew W. C. Robinson et al. Epoxide ring-opening and Meinwald rearrangement reactions of epoxides catalyzed by mesoporous aluminosilicates. Org. Biomol. Chem. 2009, 7, 2559-2564.
Kandasamy Jeyakumar et al. Ring-Opening Reactions of Epoxides Catalyzed by Molybdenum(VI) Dichloride Dioxide. Synthesis, 2008, 5, 807-819.
Thierry K Slot et al. Enhancing catalytic epoxide ring-opening selectivity using surface-modified Ti3C2Tx MXenes. 2D Mater. 2021, 8, 035003.
Ricardo F. Mendes et al. A Lamellar Coordination Polymer with Remarkable Catalytic Activity. Chem. Eur. J. 2016, 22, 13136-13146.
Patricia Silva et al. Thermal Transformation of a Layered Multifunctional Network into a Metal-Organic Framework Based on a Polymeric Organic Linker. J. Am. Chem. Soc. 2011, 133, 15120-15138.
Amarajothi Dhakshinamoorthy et al. Metal-Organic Frameworks as Efficient Heterogeneous Catalysts for the Regioselective Ring Opening of Epoxides. Chem. Eur. J. 2010, 16, 8530-8536.
Saeideh-Sadat Mortazavi et al. A new Brønsted acid MIL-101(Cr) catalyst by tandem post-functionalization; synthesis and its catalytic application. Appl. Organomet. Chem. 2020, 34, e5717.
Ricardo F. Mendes et al. Sustainable synthesis of a catalytic active one-dimensional lanthanide-organic coordination polymer. Chem. Commun. 2015, 51, 10807-10810.
Maryam Mirza-Aghayan et al. Graphite oxide: a simple and efficient solid acid catalyst for the ring-opening of epoxides by alcohols. Tetrahedron Letters, 2014, 55, 6694-6697.
Xiaoting Jing et al. Polyoxometalate-modified reduced graphene oxide foam as a monolith reactor for efficient flow catalysis of epoxide ring-opening reactions. J. Mater. Chem. A, 2021, 9, 8480-8488.
Carlos J. Duran-Valle et al. Acidic Activated Carbons: An Efficient Catalyst for the Epoxide Ring-Opening Reaction with Ethanol. Catal. Lett. 2009, 130, 37-41.
Inês Matos et al. Mesoporous carbon as an efficient catalyst for alcoholysis and aminolysis of epoxides. Applied Catalysis A: General, 2012, 439-440, 24-30.
Mathew W.C. Robinson et al. Synthesis and catalytic activity of nanoporous aluminosilicate materials. Journal of Molecular Catalysis A: Chemical, 2009, 314, 10-14.
Sandeep S. Kahandal et al. Sulphated yttria-zirconia as a regioselective catalyst system for the alcoholysis of epoxides. Catal. Sci. Technol. 2012, 2, 1493-1499.
Lihong Zhang et al. Sulfur and iron co-doped titanoniobate nanosheets: a novel efficient solid acid catalyst for alcoholysis of styrene epoxide at room temperature. Chem. Commun. 2013, 49, 7507-7509.
Federica Zaccheria et al. CuO/SiO2: a simple and efficient solid acid catalyst for epoxide ring opening. Green Chem. 2011, 13, 545.
Vaibhav R. Acham et al. An epoxide ring-opening reaction by using sol-gel-synthesized palladium supported on a strontium hydroxyl fluoride catalyst. C. R. Chimie, 2016, 19, 1237-1246.
Sayantani Das et al. Epoxide Ring-Opening Reactions with Mesoporous Silica-Supported Fe(III) Catalysts. ACS Catal. 2011, 1, 502-510.
Lin Chen et al. Metal boride better than Pt: HCP Pd2B as a superactive hydrogen evolution reaction catalyst. Energy Environ. Sci. 2019, 12, 3099-3105.
Michelle M. Flores Espinosa et al. Compressed Intermetallic Pdcu for Enhanced Electrocatalysis. ACS Energy Lett. 2020, 5, 3672-3680.
Tingting Chao et al. Atomically Dispersed Copper-Platinum Dual Sites Alloyed with Palladium Nanorings Catalyze the Hydrogen Evolution Reaction. Angew. Chem. 2017, 56, 16047-16051.
Zhanxi Fan et al. Synthesis of 4H/fcc Noble Multimetallic Nanoribbons for Electrocatalytic Hydrogen Evolution Reaction. J. Am. Chem. Soc. 2016, 138, 1414-1419.
Fang Luo et al. Palladium Phosphide as a Stable and Efficient Electrocatalyst for Overall Water Splitting. Angew. Chem. Int. Ed. 2018, 57, 14862-14867.
Yanyan Jia et al. Stable Pd—Cu Hydride Catalyst for Efficient Hydrogen Evolution. Nano Lett. 2022, 22, 1391-1397.
Suli Liu et al. Cation vacancy-modulated PtPdRuTe five-fold twinned nanomaterial for catalyzing hydrogen evolution reaction. Nano Energy, 2019, 61, 346-351.
Lixin Jiao et al. Ultrathin PdTe nanowires anchoring reduced graphene oxide cathodes for efficient hydrogen evolution reaction. Nanoscale, 2015, 7, 18441-18445.
Xinxin Yang et al. An amorphous nanoporous PdCuNi—S hybrid electrocatalyst for highly efficient hydrogen production. Applied Catalysis B: Environmental, 2019, 246, 156-165.
Tanmay Bhowmik et al. Palladium Nanoparticle-Graphitic Carbon Nitride Porous Synergistic Catalyst for Hydrogen Evolution/Oxidation Reactions over a Broad Range of pH and Correlation of Its Catalytic Activity with Measured Hydrogen Binding Energy. ACS Catal. 2016, 6, 1929-1941.
Jing Li et al. Pdcu@Pd Nanocube with Pt-Like Activity for Hydrogen Evolution Reaction. ACS Appl. Mater. Interfaces, 2017, 9, 8151-8160.
Jitang Chen et al. Active and Durable Hydrogen Evolution Reaction Catalyst Derived from Pd-Doped Metal-Organic Frameworks. ACS Appl. Mater. Interfaces, 2016, 8, 13378-13383.
Yaping Li et al. Near-surface dilution of trace Pd atoms to facilitate Pd—H bond cleavage for giant enhancement of electrocatalytic hydrogen evolution. Nano Energy, 2017, 34, 306-312.
Lijun Zheng et al. Palladium/Bismuth/Copper Hierarchical Nano-Architectures for Efficient Hydrogen Evolution and Stable Hydrogen Detection. Acs Appl. Mater. Interfaces, 2019, 11, 6248-6256.
X. Zeng et al. Mesoporous TiO2 nanospheres loaded with highly dispersed Pd nanoparticles for pH-universal hydrogen evolution reaction. Materials Today Nano, 2019, 6, 100038.
Zhicheng Zhang et al. Evoking ordered vacancies in metallic nanostructures toward a vacated Barlow packing for high-performance hydrogen evolution. Sci. Adv. 2021, 7, eabd6647.
Jiawei Liu et al. Selective Epitaxial Growth of Rh Nanorods on 2H/fcc Heterophase Au Nanosheets to Form 1D/2D Rh—Au Heterostructures for Highly Efficient Hydrogen Evolution. J. Am. Chem. Soc. 2021, 143, 4387-4396.
Yao Zheng et al. High Electrocatalytic Hydrogen Evolution Activity of an Anomalous Ruthenium Catalyst. J. Am. Chem Soc. 2016, 138, 16174-16181.
Feng Li et al. Balancing hydrogen adsorption/desorption by orbital modulation for efficient hydrogen evolution catalysis. Nature Communiations, 2019, 10, 4060.
Javeed Mahmood et al. An efficient and pH-universal ruthenium-based catalyst for the hydrogen evolution reaction. Nature Nanotechnology, 2017, 12, 441-446.
C. Yang et al. Engineering nanoporous Ag/Pd core/shell interfaces with ultrathin Pt doping for efficient hydrogen evolution reaction over a wide pH range. J. Mater. Chem. A, 2018, 6, 14281-14290.
Yang Yang et al. O-coordinated W—Mo dual-atom catalyst for pH-universal electrocatalytic hydrogen evolution. Sci. Adv. 2020, 6, eaba6586.
Qin Yang et al. Single Carbon Vacancy Traps Atomic Platinum for Hydrogen Evolution Catalysis. J. Am. Chem. Soc. 2022, 144, 2171-2178.
Yucai Wu et al. Anchoring Sub-Nanometer Pt Clusters on Crumpled Paper-Like Mxene Enables High Hydrogen Evolution Mass Activity. Adv. Funct. Mater. 2022, 32, 2110910.
Yiyao Ge et al. Synthesis of amorphous Pd-based nanocatalysts for efficient alcoholysis of styrene oxide and electrochemical hydrogen

(56) References Cited

OTHER PUBLICATIONS evolution. Nano Res. 2022, https://doi.org/10.1007/s12274-022-5101-0.

* cited by examiner

| | Ru at% | Rh at% |
|---|---|---|
| EDS | 10.1 at% | 10.9 at% |
| ICP | 12.0 at% | 10.8 at% |

METHOD FOR SYNTHESIZING AMORPHOUS Pd-BASED NANOPARTICLES

CROSS-REFERENCE WITH OTHER APPLICATIONS

The present application claims priority to the U.S. Provisional Patent Application No. 63/334,655 filed 25 Apr. 2022; the disclosure of which is incorporated herein by reference in its entirety.

FIELD OF THE INVENTION

The present invention generally relates to synthesis of noble metal nanomaterials and catalytic applications of the same. More specifically, the present invention relates to synthesis of amorphous palladium (Pd)-based nanoparticles and catalytic applications of the same.

BACKGROUND OF THE INVENTION

Noble metal nanomaterials normally serve as efficient catalysts for various important reactions in pharmaceutical, chemical industries, such as ring-opening reactions of epoxides. Linear and/or branched alcohols in epoxides can be formed via the selective hydrogenation route, which is normally catalyzed by metals under hydrogen ($H_2$) atmosphere; when alcohols exist as nucleophiles, the alcoholysis reaction of epoxides could occur to predominantly obtain the branched β-alkoxy alcohols, which is mainly catalyzed by homogeneous catalysts, in general suffering from the inherent drawbacks such as catalyst recycling and production purification. As illustrated in FIG. 1, the alcoholysis reaction and hydrogenation reaction could compete against each other in the ring-opening reaction of SO in ethanol under $H_2$ atmosphere. It still remains a key challenge to efficiently switch the ring-opening route of SO for the highly selective synthesis of distinct targeted chemicals.

Among the noble metals, Pd-based nanomaterials have drawn particular attention and been extensively studied for decades due to their high intrinsic activities towards diverse catalytic applications. Previous research results also indicated that Pd-based nanoalloy materials with multi-metal components could exhibit significantly improved catalytic performance compared with single metals due to the synergistic effect between different metal atoms. However, most of the previous works on Pd-based catalysts only focused on the thermodynamically stable conventional crystalline phase, i.e., face-centered cubic (fcc) phase. Recently, the rapid progress made in the field of phase engineering of nanomaterials (PEN) has revealed that the phase structure, i.e., atomic arrangement, of nanomaterials plays a vital role in determining their properties and functions. Some studies have demonstrated that noble metal nanomaterials with unconventional phases, in comparison with their counterpart with conventional phase structures, could exhibit distinct physicochemical properties and catalytic performance.

In particular, nanomaterials with amorphous phase, i.e., long-range disordered structure, have emerged as new, highly efficient catalysts due to the abundant uncoordinated sites and dangling bonds. To date, several synthetic approaches have been developed to prepare amorphous noble metal nanomaterials, which exhibited excellent performance towards various catalytic reactions, e.g., thermal annealing synthesis of amorphous Ir nanosheets for electrochemical oxygen evolution, template-assistant synthesis of amorphous Au nanoclusters for electrocatalytic carbon dioxide reduction.

However, the rational preparation of amorphous noble metal nanomaterials still remains difficult due to the strong metallic bonds existed between atoms of noble metals. Therefore, it is of importance to develop controllable and general strategies to realize the controlled synthesis of amorphous noble metal and their alloy nanomaterials with tunable compositions for development of high performance catalysts.

SUMMARY OF THE INVENTION

It is an objective of the present invention to provide a robust and controlled approach for synthesizing amorphous Pd-based nanomaterials which can be used as catalysts with high efficiency, high selectivity, low overpotential and high turnover frequency in various catalytic reactions.

In accordance with a first aspect of the present invention, a method for synthesizing amorphous Pd-based nanoparticles is provided. The provided method comprises: a) dissolving a Pd precursor in a first solvent to form a first solution; b) mixing the first solution with a second solvent to form a first mixture; c) adding surfactant into the first mixture to form a second mixture; d) heating the second mixture at a first heating temperature for a first heating time to render a second solution; e) adding other metal precursor into the second solution to form a third mixture; f) heating the third mixture at a second heating temperature for a second heating time to render a third solution; g) naturally cooling down the third solution to a room temperature; h) adding ethanol to the third solution to form a fourth solution; and i) collecting the amorphous Pd-based nanoparticles from the fourth solution by centrifugation.

The Pd precursor is Pd(II) acetylacetonate, Pd(II) acetate, $PdBr_2$ or combinations thereof.

The Pd precursor has a purity of greater than or equal to 98%; the first solvent is a toluene having a purity of greater than or equal to 99.5. Preferably, the concentration of Pd precursor in the toluene is 10 mg/ml.

The second solvent is an oleylamine having a purity greater than or equal to 70%; and a volume ratio of the oleylamine to the first solution is in a range from 20:1 to 3:1. Preferably, the volume ratio of the oleylamine to the first solution is 9:1.

The surfactant is a $C_3$-$C_{20}$ alkanethiol, an organophosphorus compound or the combination thereof. The amorphous Pd-based nanoparticles synthesized using alkanethiol as surfactant have a particle size of 4 nm to 8 nm. The amorphous Pd-based nanoparticles synthesized using organophosphorus compound as surfactant have a particle size of 8 nm to 12 nm.

The surfactant is 1-propanethiol, 1-octanethiol, 2-ethylhexanethiol, 1-dodecanethiol, 1-tetradecanethiol, 1-hexadecanethiol, 1-octadecanethiol, triphenylphosphine, trioctylphosphine, or combinations thereof.

The surfactant has a purity greater than or equal to 98%; and a molar ratio of the surfactant to Pd precursor is in a range from 1:2 to 2:1. Preferably, the molar ratio of the surfactant to Pd precursor is 1:1.

The first heating temperature is in a range from 140° C. to 200° C.; and the first heating time is in a range from 15 to 25 minutes. Preferably, the first heating temperature is 155° C.; and the first heating time is 20 minutes.

The other metal precursor is a ruthenium (Ru) precursor, a rhodium (Rh) precursor, an silver (Ag) precursor, an iridium (Ir) precursor, a nickel (Ni) precursor or combinations thereof.

The other metal precursor has a purity greater than or equal to 99.98%; and a molar ratio of the other metal precursor to the Pd precursor is in a range from 1:10 to 1:1.

The molar ratio of the other metal precursor to the Pd precursor is 1:2.

The step e) further comprising dissolving the other metal precursor in a solvent before adding the other metal precursor into the second solution.

The second heating temperature is in a range from 140° C. to 200° C.; and the second heating time is in a range from 45 to 75 minutes.

The second heating temperature is 155° C.; and the second heating time is 60 minutes.

The volume ratio of the ethanol to the third solution is in a range from 1:1 to 5:1.

In accordance with a second aspect of the present invention, a method of preparing a catalyst using amorphous Pd-based nanoparticles is provided. The method comprises: synthesizing amorphous Pd-based nanoparticles with the method in accordance with the first aspect of the present invention; dispersing carbon powder in ethanol to obtain a fourth mixture; sonicating the fourth mixture in an ice bath for one hour to form a carbon suspension; adding the synthesized amorphous Pd-based nanoparticles into the carbon suspension to obtain a fifth mixture; sonicating the fifth mixture in an ice bath for one hour to form a catalyst-loaded carbon suspension; collecting the catalyst-loaded carbon from the catalyst-loaded carbon suspension by centrifugation; washing the catalyst-loaded carbon with a mixture solution composing of chloroform and ethanol; re-dispersing the catalyst-loaded carbon in a mixture solution containing isopropanol and water to form a sixth mixture; adding sulfonated tetrafluoroethylene based fluoropolymer-copolymer dispersion (i.e., Nafion™ solution) into the sixth mixture to form a seventh mixture; and sonicating the seventh mixture in an ice bath for one hour to form a catalyst.

In accordance with a third aspect of the present invention, a method of using amorphous Pd-based nanoparticles as catalysts for electrochemical hydrogen evolution reaction or ring-opening reaction of an epoxide is provided.

The provided synthesis method allows tuning of the phase of Pd-based nanocatalysts for efficiently switching the ring-opening route of SO for the synthesis of distinct targeted chemicals and also modulating of catalytic performance thereof towards electrochemical HER. Specifically, the usage of amorphous Pd-based alloy nanocatalyst (e.g., Pd, PdRu alloy nanoparticles) induces the alcoholysis reaction of SO towards the highly selective production of 2-ethoxy-2-phenylethanol (EPE), while the conventional crystalline Pd-based catalyst (e.g., fcc-Pd, fcc-PdRu alloy nanoparticles) mainly catalyzes the hydrogenation reaction of SO to form 2-phenylethanol (PE) with high selectivity..

Pd-based catalysts can also be applied in various electrochemical reactions such as HER. In present invention, the amorphous PdRh nanocatalyst (e.g., Pd, PdRu alloy nanoparticles) exhibits significantly superior HER performance with lower overpotential and higher turnover frequency (TOF) values compared to the counterpart crystalline fcc-Pd-based catalyst. The conventional crystalline fcc-Pd-based catalyst, in which binding between Pd and hydrogen during the HER process is normally too strong, the amorphous Pd-based nanomaterials could exhibit weakened binding towards hydrogen due to the modified electronic structure, which leads to the enhanced HER performance. Besides, the amorphous structures could possess abundant dangling bonds and uncoordinated atoms, which provide more active sites for catalytic reactions, facilitating the HER process. In addition, the excellent HER activity of binary amorphous PdRh catalyst could also be attributed to the alloying effect of Pd and Rh. Specifically, the synergistic effect between Rh and Pd atoms could efficiently modify the electronic structure of Pd and weaken the adsorption of hydrogen on Pd, thus boosting the HER performance.

BRIEF DESCRIPTION OF THE DRAWINGS

Embodiments of the invention are described in more details hereinafter with reference to the drawings, in which.

DETAILED DESCRIPTION

In the following description, a method for synthesizing amorphous Pd-based nanoparticles and the likes are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

Figure 1:
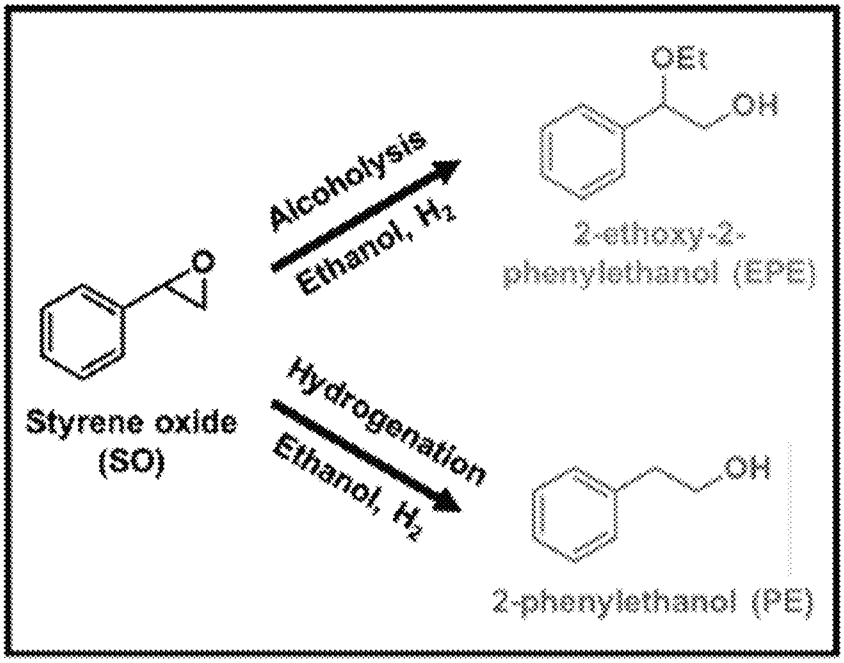
FIG. 1 illustrates two typical ring-opening reaction routes of SO via an alcoholysis reaction and hydrogenation reaction to produce EPE and PE, respectively.
Figure 2:
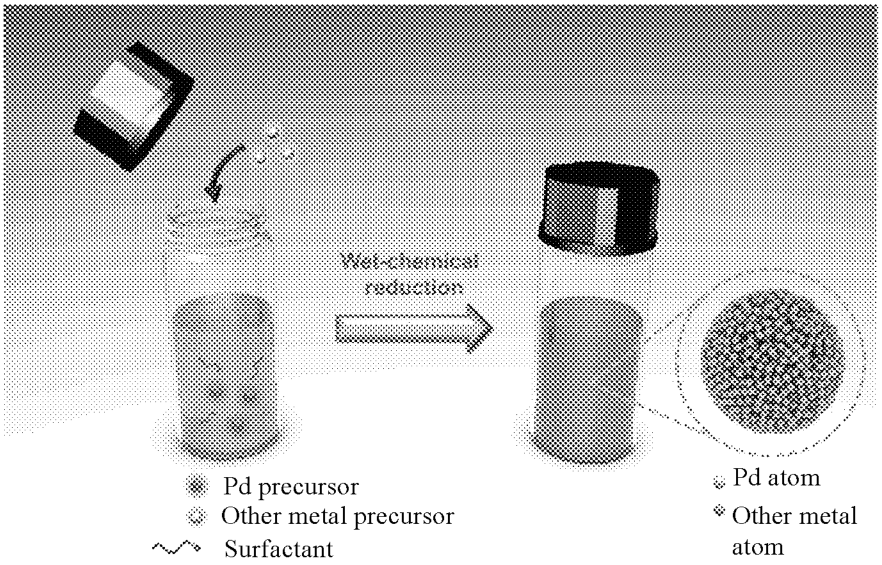
FIG. 2 illustrates the preparation process of amorphous Pd-based nanoparticles (NPs) through a one-pot reduction method by adding other metal precursors.

Referring to FIG. 2, in accordance with some embodiments of the present invention, a series of amorphous Pd-based nanoparticles may be synthesized via a facile one-pot wet-chemical approach. In particular, a Pd precursor is dissolved in a first solvent, to form a first solution; the first solution is mixed with a second solvent to form a first mixture; surfactant is added into the first mixture to form a second mixture; the second mixture is undergone a first heat treatment to render a second solution; other metal precursor is then added into the second solution to form a third mixture; the third mixture is undergone a second heat treatment to render a third solution; the third solution is naturally cooled down to a room temperature; ethanol is added to the third solution to form a fourth solution; and the amorphous Pd-based nanoparticles are collected from the fourth solution by centrifugation.

In some embodiments, the amorphous Pd-based nanoparticles are washed after being precipitated from the fourth solution. Particularly, the washing step includes dispersing the amorphous Pd-based nanoparticles into a third solvent and sonicating the solution, adding a fourth solvent and sonicating the mixture, and collecting the solid product by centrifugation. The third solvent is different from the fourth solvent. Preferably, the third solvent is selected from the group consisting of chloroform, hexane and toluene, and the fourth solvent is selected from the group consisting of ethanol, methanol and acetone.

The amorphous Pd-based nanoparticles may be, but are not limited to, binary, ternary, quaternary or quinary amorphous Pd-based nanoparticles. More particularly, the amorphous Pd-based nanoparticles may be, but not limited to, amorphous Pd—Ru, Pd—Ag, Pd—Rh, Pd—Ir, Pd—Ni, Pd—Ag—Ru, Pd—Ag—Rh, Pd—Ru—Rh, Pd—Ag—Ru—Rh or Pd—Ag—Ru—Rh—Ir nanoparticles.

The first solvent may be, but not limited to, a toluene, an ethanol, a methanol, a chloroform or combinations thereof.

The second solvent may be, but not limited to, an amine, an alkene or combinations thereof.

EXAMPLES

Synthesis of a-PdRu NPs

In a typical synthesis, 40.5 mg of $Pd(OAc)_2$ were dissolved in 4.05 mL of toluene and then mixed with 36 mL of oleylamine in a 50-mL vial under magnetic stirring. After 45 μL of 1-dodecanethiol were added, the mixture was stirred for another 15 min at room temperature. The vial was then immersed into an oil bath at 155° C. and kept for 20 min. Subsequently, 27.9 mg of $RuCl_3 \cdot {}_\chi H_2O$ (dissolved in 2.79 mL of ethanol) were added into the reaction solution. After holding at 155° C. for another 60 min, the vial was taken out, followed by naturally cooling down to room temperature. After adding 70 mL of ethanol, the product was collected by centrifugation at 10,000 rpm for 10 min. After the as-obtained a-PdRu NPs were dispersed into 15 mL of chloroform and sonicated for 5 min, 90 mL of acetone were added to precipitate the NPs. The a-PdRu NPs were then collected by centrifugation at 10,000 rpm for 10 min. The aforementioned washing process was repeated for three times. Finally, the a-PdRu NPs were re-dispersed in toluene for further usage.

Synthesis of a-PdRh NPs

The synthesis protocol of a-PdRh NPs is basically the same as the aforesaid protocol for the preparation of a-PdRu NPs except changing the added metal precursor from 27.9 mg of $RuCl_3 \cdot {}_\chi H_2O$ to 25.2 mg of $RhCl_3 \cdot {}_\chi H_2O$ (dissolved in 2.52 mL of ethanol). After washing by following the same protocol for three times, the obtained a-PdRh NPs were finally re-dispersed in toluene for further usage.

Synthesis a-PdRuRh NPs

The synthesis protocol of a-PdRuRh NPs is basically the same protocol for the preparation of a-PdRu NPs except changing the added metal precursor from 27.9 mg of $RuCl_3 \cdot {}_\chi H_2O$ to the mixture of 27.9 mg of $RuCl_3 \cdot {}_\chi H_2O$ (dissolved in 2.79 mL of ethanol) and 25.2 mg of $RhCl_3 \cdot {}_\chi H_2O$ (dissolved in 2.52 mL of ethanol). After washing by following the same protocol for three times, the obtained a-PdRuRh NPs were finally re-dispersed in toluene for further usage.

Characterization Methodologies

TEM images, SAED patterns, and EDS data were obtained on a JEOL JEM-2100F (JEOL, Tokyo, Japan) transmission electron microscope. XRD patterns were recorded with a Siemens D500 X-ray diffractometer (Bruker AXS), using CuKa radiation (λ=1.5406 Å). The samples used for XRD characterization were prepared by drop-casting the corresponding solutions on clean glass substrates and drying under ambient conditions. XPS measurements were conducted on the ESCALAB 250Xi (Thermo Fisher Scientific) instrument. The C 1s peak with a binding energy of 284.8 eV was used as the reference. The samples used for XPS characterization were prepared by drop-casting the corresponding solutions on clean Si substrates and then drying under ambient conditions. Inductively coupled plasma optical emission spectroscopy (ICP-OES) measurements were performed on a Dual-view Optima 5300 DV ICP-OES system. The XANES and EXAFS spectra of Pd K-edge and Ru K-edge were performed at the 7-BM/QAS beamline of the National Synchrotron Light Source II (NSLS-II).

Characterization of a-PdRu NPs

Figure 3A:
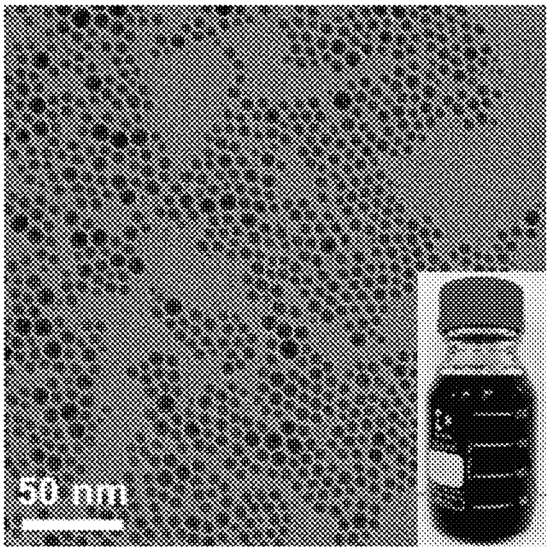
FIG. 3A is the transmission electron microscopy (TEM) image of synthesized amorphous PdRu (a-PdRu) NPs (Inset: toluene dispersion of a-PdRu NPs in a 250-mL vial).
Figure 3B:
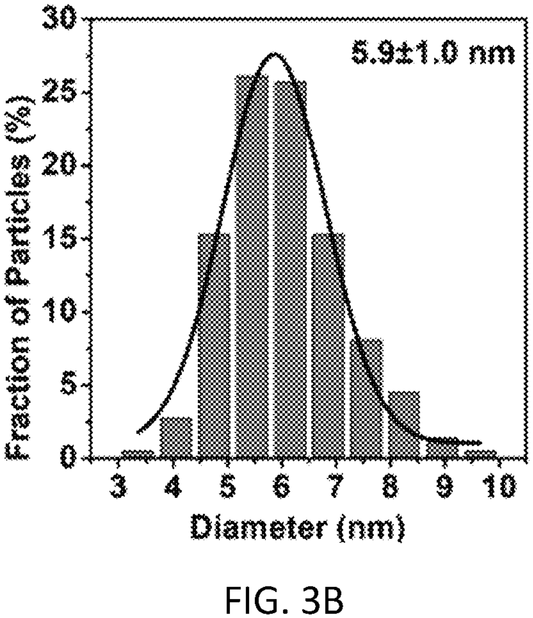
FIG. 3B is the size distribution histogram of the synthesized a-PdRu NPs.
Figure 3C:
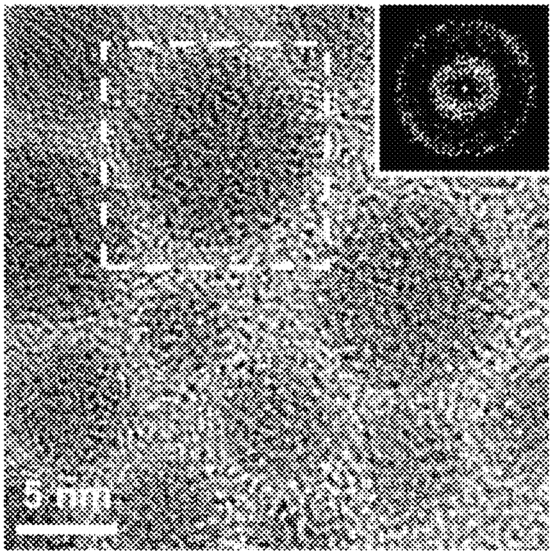
FIG. 3C is the high-resolution TEM (HRTEM) image of the synthesized a-PdRu NPs (Inset: the FFT pattern taken from the selected dashed square area).
Figure 3D:
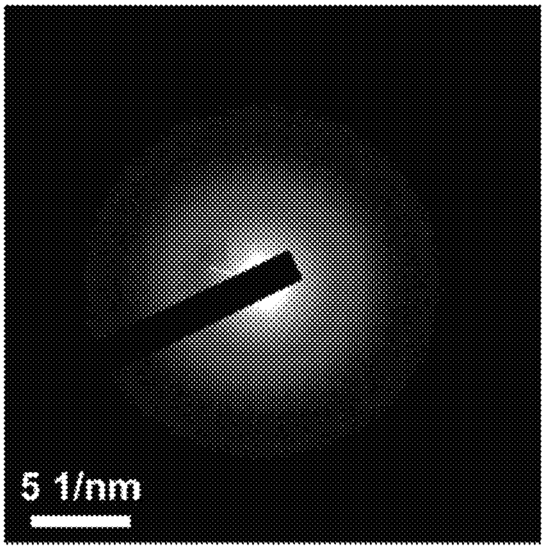
FIG. 3D is the selected area electron diffraction (SAED) pattern of the synthesized a-PdRu NPs.
Figure 3E:
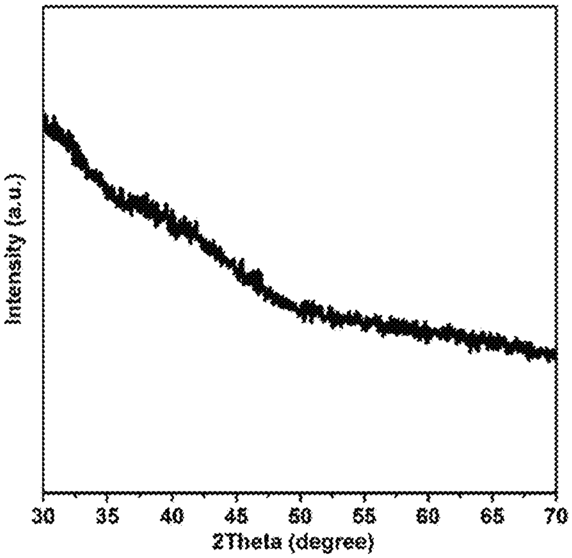
FIG. 3E is the X-ray diffraction (XRD) pattern of the synthesized a-PdRu NPs.
Figure 3F:
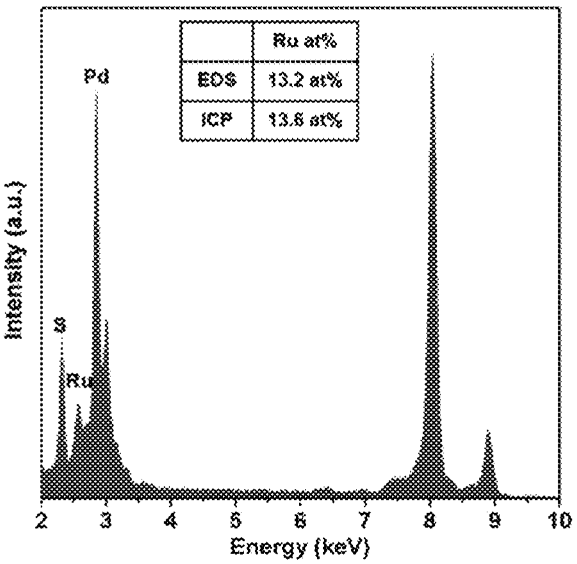
FIG. 3F is the energy disperse X-ray spectroscopy (EDS) and inductively coupled plasma optical emission spectroscopy (ICP-OES) characterizations of the synthesized a-PdRu NPs.
Figure 3G:
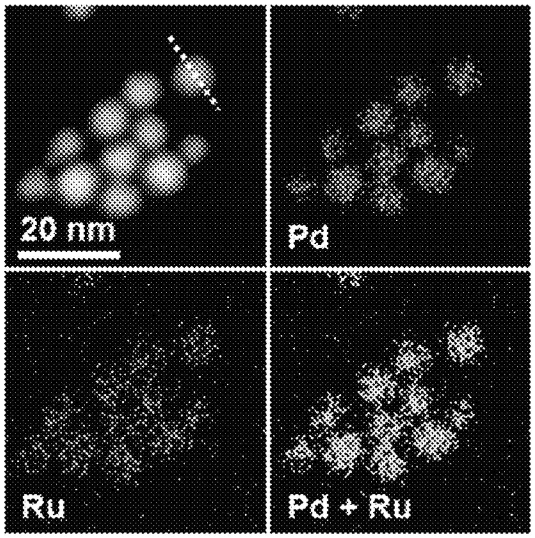
FIG. 3G is the scanning transmission electron microscope (STEM) image of the synthesized a-PdRu NPs and the corresponding EDS elemental mappings.
Figure 3H:
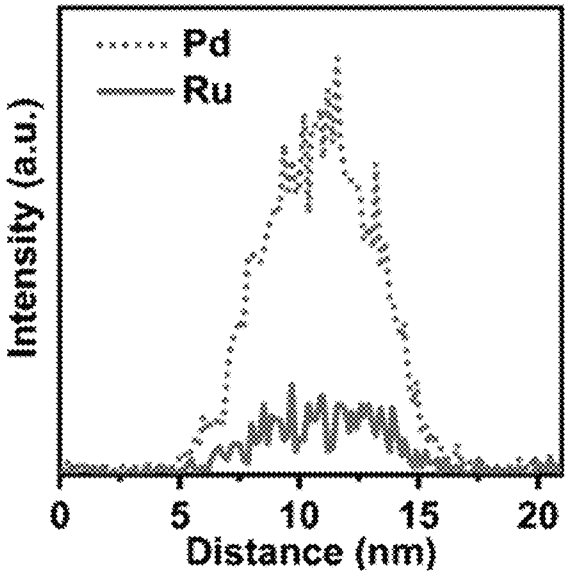
FIG. 3H is the EDS elemental line scan along the dotted white line in FIG. 3G.

As shown in the TEM image in FIG. 3A and the size distribution histogram in FIG. 3B, the obtained a-PdRu NPs are quasi-spherical with a size of 5.9±1.0 nm. The HRTEM image (FIG. 3C) clearly shows the long-range disordered atomic arrangement in a-PdRu NPs. The diffuse rings in the corresponding selected-area fast Fourier transform (FFT) pattern (inset of FIG. 3C) and SAED pattern (FIG. 3D) further confirm the amorphous structure of obtained a-PdRu NPs. XRD was also used to characterize the crystallinity of as-synthesized NPs. As shown in FIG. 3E, no obvious diffraction peak is observed in the XRD pattern of a-PdRu NPs, corroborating their amorphous phase. EDS analysis (FIG. 3F) reveals that the atomic percentage of Ru in a-PdRu NPs is determined to be 13.2 at %, which is consistent with the value of 13.6 at % based on the ICP-OES result. EDS elemental mappings (FIG. 3G) and line scan (FIG. 3H) corroborate the distribution of Pd and Ru elements, verifying the alloy structure of a-PdRu NPs.

Figure 3I:
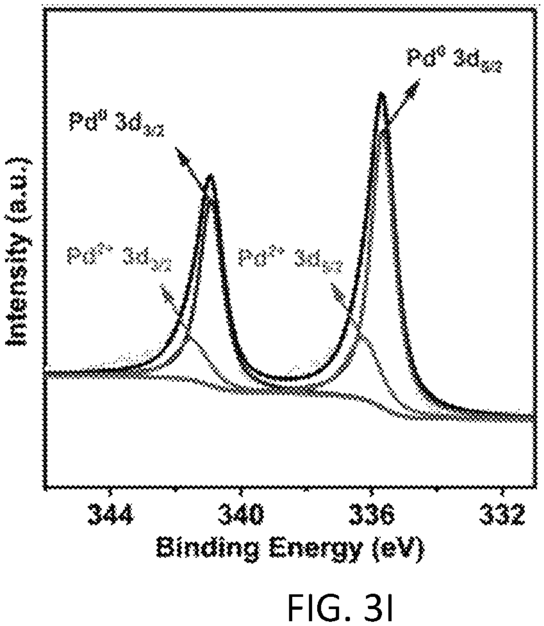
FIG. 3I is the Pd 3d X-ray photoelectron spectroscopy (XPS) spectrum of the synthesized a-PdRu NPs.
Figure 3J:
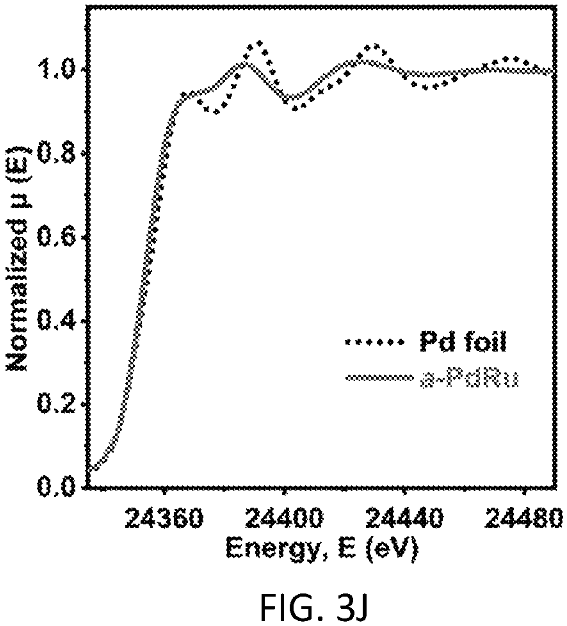
FIG. 3J is the Pd K-edge X-ray absorption near edge structure (XANES) spectra of the synthesized a-PdRu NPs and commercial Pd foil.
Figure 3K:
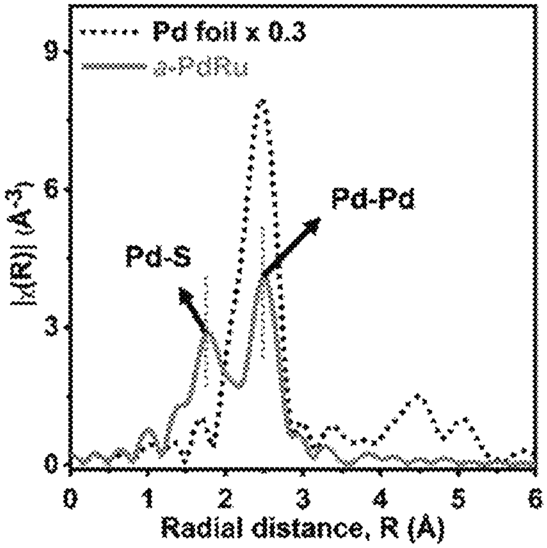
FIG. 3K is the Pd K-edge Fourier-transformed extended X-ray absorption fine structure (EXAFS) spectra of the synthesized a-PdRu NPs and commercial Pd foil.
Figure 3L:
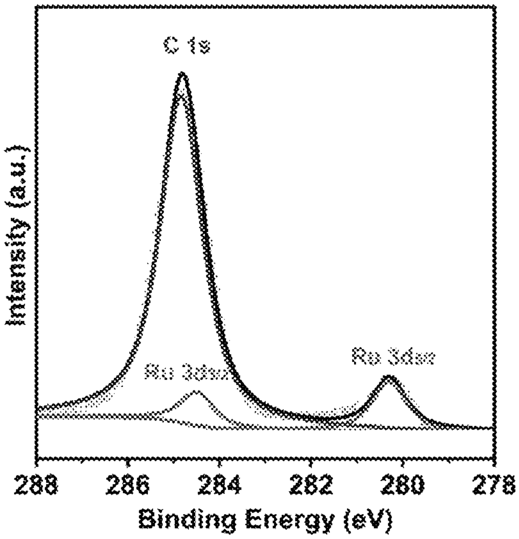
FIG. 3L is the Ru 3d XPS spectrum of the synthesized a-PdRu NPs.
Figure 3M:
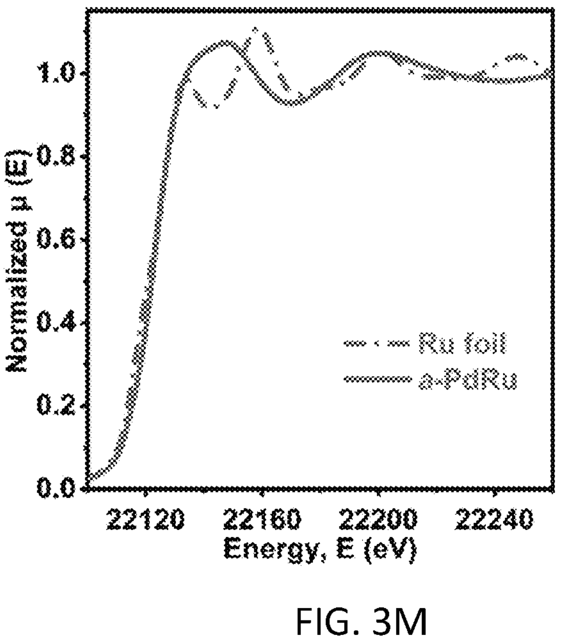
FIG. 3M is the Ru K-edge XANES spectra of the synthesized a-PdRu NPs and commercial Ru foil.
Figure 3N:
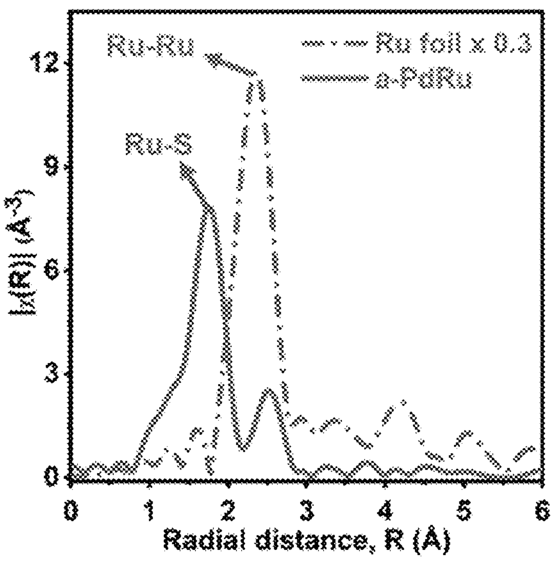
FIG. 3N is the Ru K-edge Fourier-transformed EXAFS spectra of the synthesized a-PdRu NPs and commercial Ru foil.

XPS and XAFS characterizations were carried out to study the chemical states and electronic structures of Pd and Ru in the synthesized a-PdRu NPs. As shown in FIG. 3I, two main fitted peaks in the Pd 3d spectrum of a-PdRu NPs correspond to $Pd^0$, while two weak peaks corresponding to $Pd^{2+}$ can also be observed, demonstrating the mixed chemical states of Pd element. The presence of $Pd^{2+}$ 3d peaks could be ascribed to the formation of Pd—S bond on the surface of a-PdRu NPs due to the strong interaction between Pd atoms and S atoms in thiol molecules. The XANES spectrum (FIG. 3J) and the corresponding Fourier-transformed EXAFS spectrum (FIG. 3K) of the Pd K-edge confirm the presence of both Pd—Pd and Pd—S bonds in the a-PdRu NPs, further corroborating the mixed chemical states of Pd element, which shows good agreement with the XPS result (FIG. 3I). It is worth mentioning that the formation of strong Pd—S bond on the surface of Pd could facilitate the formation of amorphous structure. Moreover, the Ru 3d XPS profile (FIG. 3L), the Ru K-edge XANES spectrum (FIG. 3M), and the corresponding EXAFS spectrum (FIG. 3N) reveal the formation of Ru-S bond in the a-PdRu NPs which are mainly due to the interaction between thiol molecules and Ru atoms. In the Ru 3d XPS spectrum (FIG. 3L), the signals of Ru 3d peaks are overlapped with that of C 1s, making it difficult to clearly distinguish the chemical state of Ru solely based on the XPS characterization. The X-ray absorption fine structure (XAFS) characterizations of Ru K-edge (FIGS. 3M and 3N) affirm the formation of Ru—S bond and Ru-Ru bond in the as-synthesized a-PdRu NPs. In the EXAFS spectrum of a-PdRu NPs (FIG. 3N), two obvious peaks can be observed and assigned to the Ru—S bond length and Ru—Ru bond length, respectively.

Characterization of a-PdRh NPs

Figure 4A:
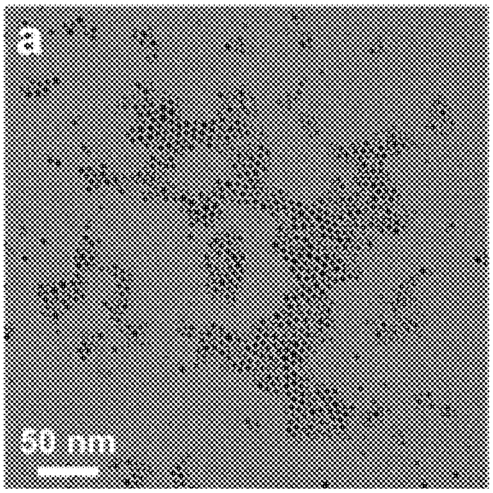
FIG. 4A is the TEM image of synthesized amorphous PdRh (a-PdRh) NPs.
Figure 4B:
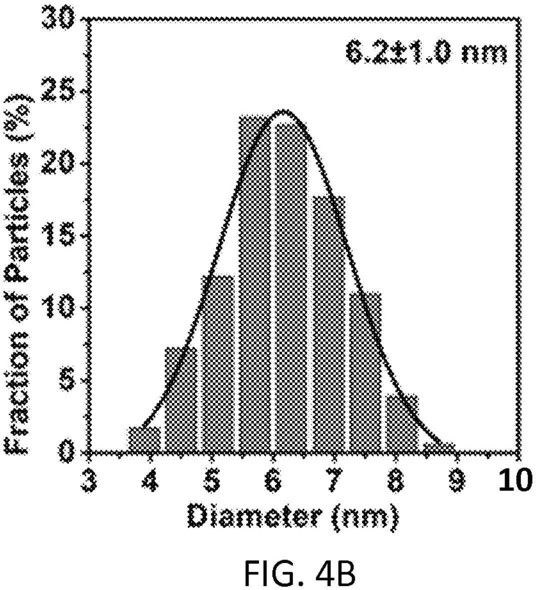
FIG. 4B is the size distribution histogram of synthesized a-PdRh NPs.
Figure 4C:
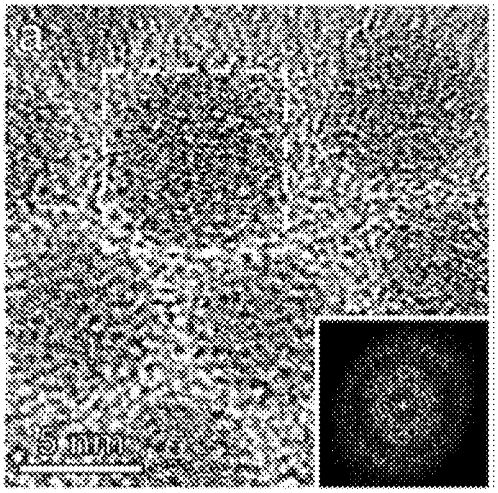
FIG. 4C is the HRTEM image of synthesized a-PdRh NPs (Inset: the corresponding FFT pattern taken from the selected dashed square area).
Figure 4D:
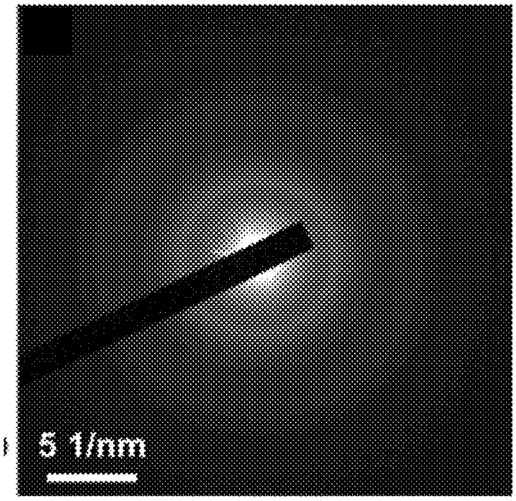
FIG. 4D is the SAED pattern of the synthesized a-PdRh NPs.
Figure 4E:
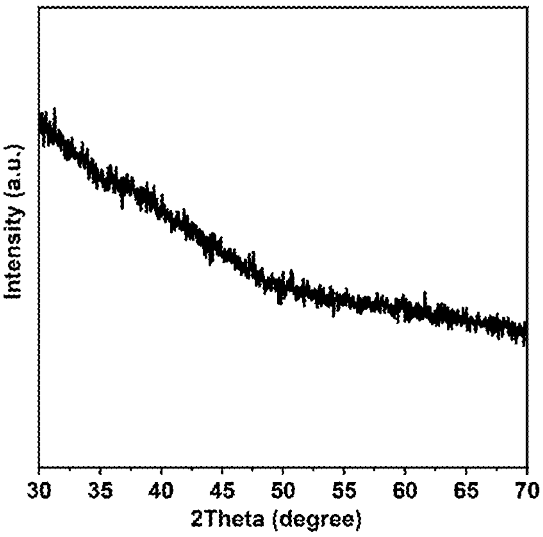
FIG. 4E is the XRD pattern of the synthesized a-PdRh NPs.
Figure 4F:
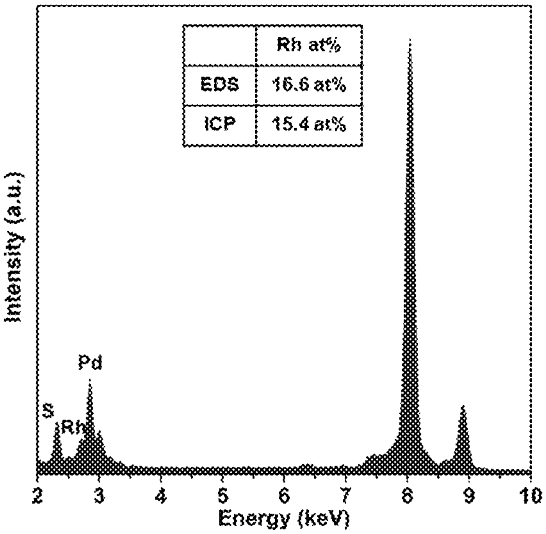
FIG. 4F is the EDS and ICP-OES characterizations of the synthesized a-PdRh NPs.
Figure 4G:
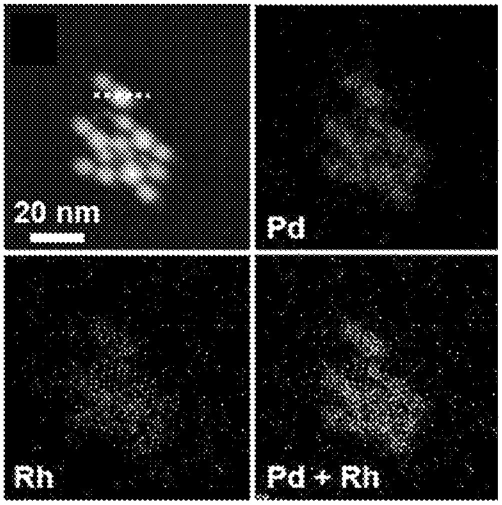
FIG. 4G is the STEM image of the synthesized a-PdRh NPs and the corresponding EDS elemental mappings.
Figure 4H:
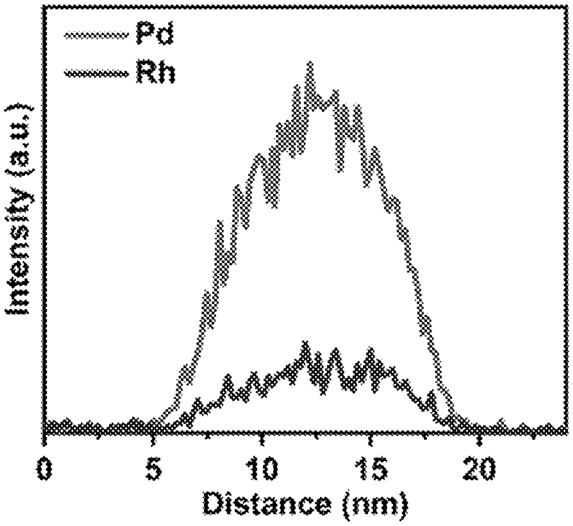
FIG. 4H is the EDS elemental line scan along the dotted white line in FIG. 4G.
Figure 4I:
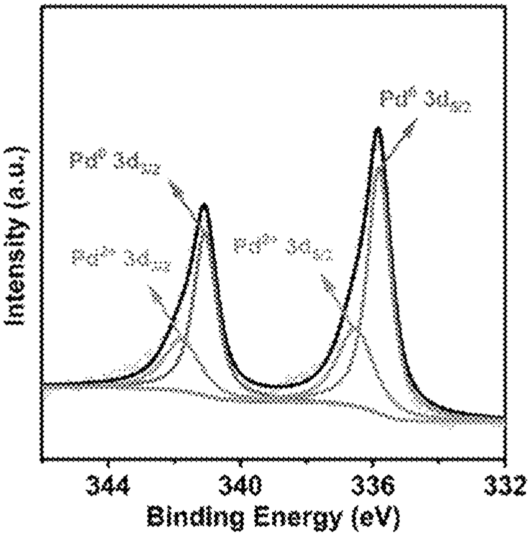
FIG. 4I is the Pd 3d XPS spectrum of the synthesized a-PdRh NPs.
Figure 4J:
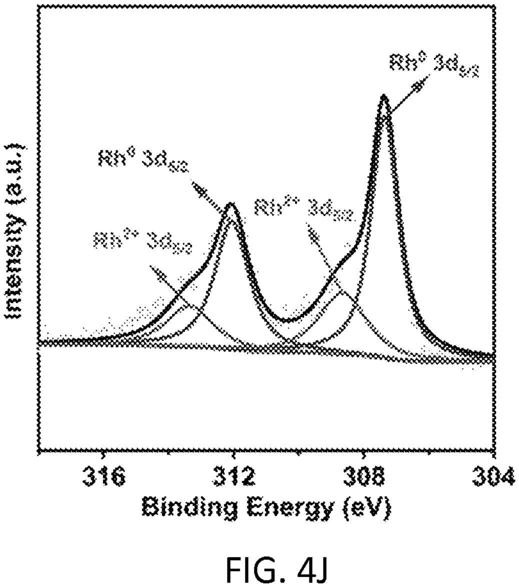
FIG. 4J is the Rh 3d XPS spectrum of the synthesized a-PdRh NPs.

The TEM image in FIG. 4A and the size distribution histogram in FIG. 4B show that the synthesized a-PdRh NPs are quasi-spherical with a size of 6.2±1.0 nm. The HRTEM image and corresponding FFT pattern (FIG. 4C and inset) demonstrate the lack of long-range ordered atomic ordering in the a-PdRh NPs. The diffuse ring in the SAED pattern (FIG. 4D) and the absence of diffraction peak in XRD profile (FIG. 4E) further affirm the amorphous phase. EDS spectrum shows that the atomic percentage of Rh in a-PdRh NPs is estimated to be 16.6 at %, similar to the value of 15.4 at % according to the ICP-OES result (FIG. 4F). The EDS elemental mappings (FIG. 4G) and line scan (FIG. 4H) reveal that Pd and Rh are evenly distributed in the obtained NPs. The XPS spectra of Pd 3d (FIG. 41) and Rh 3d (FIG. 4J) confirm that both the Pd and Rh elements possess mixed chemical states. The existence of weak peaks corresponding to $Pd^{2+}$ and $Rh^{2+}$ could mainly be attributed to the formation of Pd—S and Rh—S bonds.

Characterization of a-PdRuRh NPs

Figure 5A:
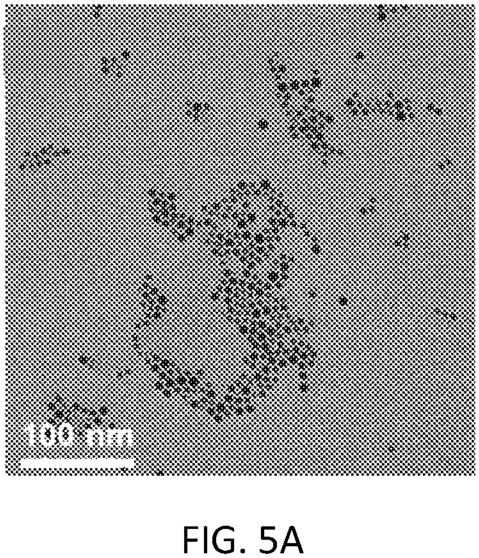
FIG. 5A is the TEM image of the synthesized amorphous PdRuRh (a-PdRuRh) NPs.
Figure 5B:
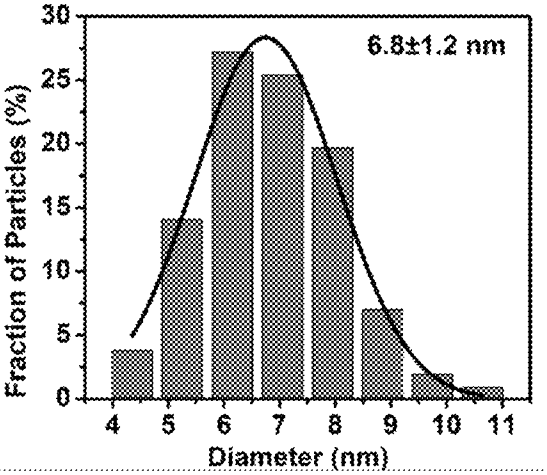
FIG. 5B is the size distribution histogram of the synthesized a-PdRuRh NPs.
Figure 5C:
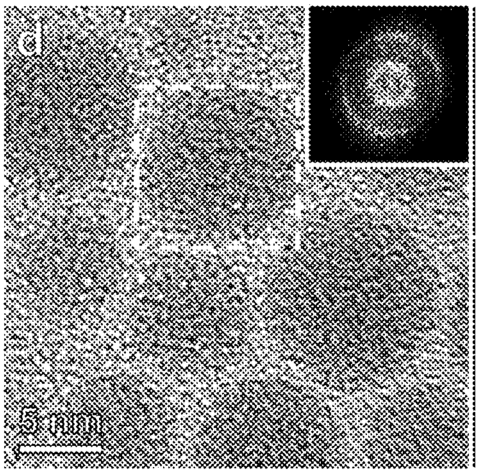
FIG. 5C is the HRTEM image of the synthesized a-PdRuRh NPs (Inset: the corresponding FFT pattern taken from the selected dashed square area).
Figure 5D:
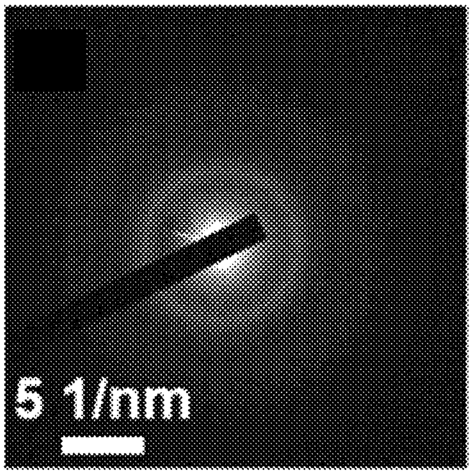
FIG. 5D is the SAED pattern of the synthesized a-PdRuRh NPs.
Figure 5E:
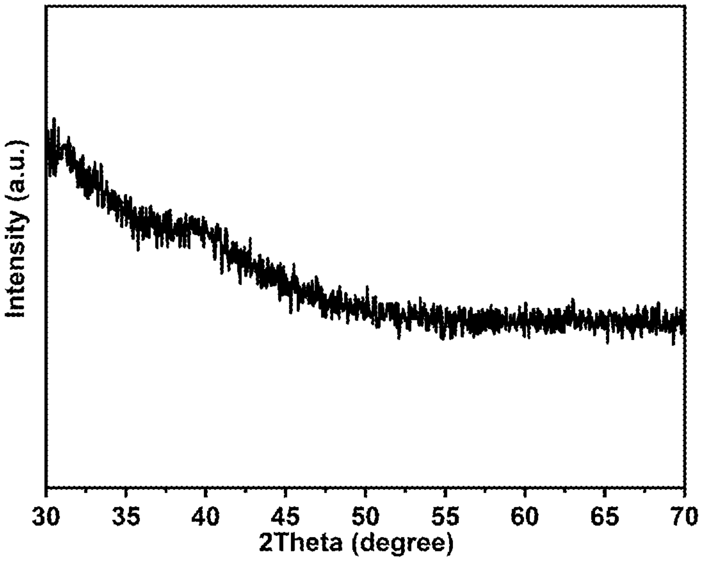
FIG. 5E is the XRD pattern of the synthesized a-PdRuRh NPs.
Figure 5F:
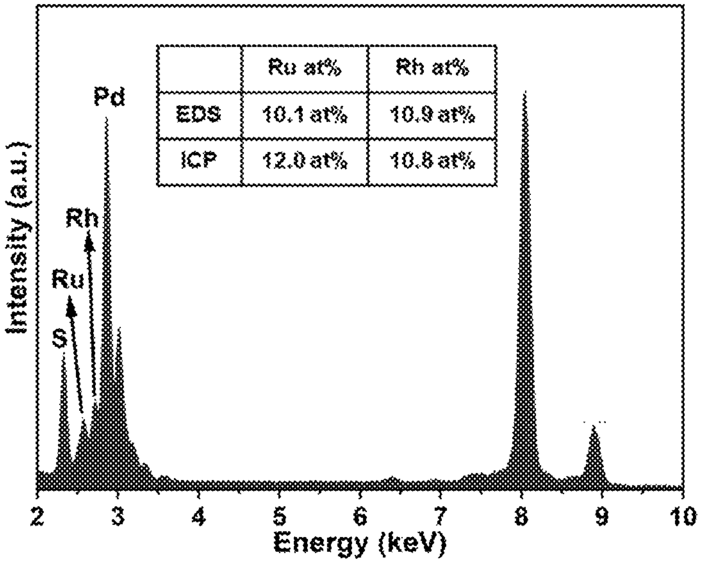
FIG. 5F is the EDS and ICP-OES characterizations of the synthesized a-PdRuRh NPs.
Figure 5G:
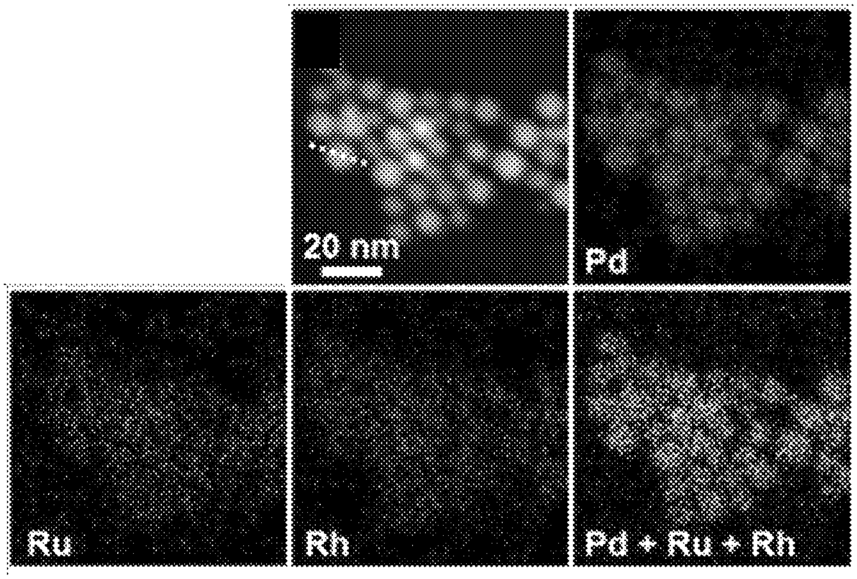
FIG. 5G is the STEM image and the corresponding EDS elemental mappings of the synthesized a-PdRuRh NPs.
Figure 5H:
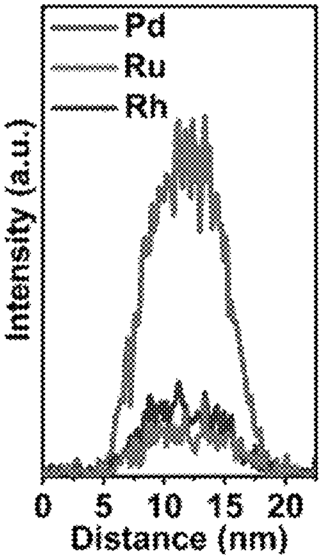
FIG. 5H is the corresponding EDS elemental line scan along the dotted white line in FIG. 5G.

The TEM image in FIG. 5A and the size distribution histogram in FIG. 5B shows that the synthesized amorphous ternary PdRuRh NPs, as referred to a-PdRuRh, possess a sphere-like morphology with a size of 6.8±1.2 nm. The disordered atomic arrangement as revealed by the HRTEM image (FIG. 5C) clearly corroborates the amorphous nature of a-PdRuRh NPs, which can be further affirmed by the diffuse rings in the FFT pattern (inset of FIG. 5C) and SAED pattern (FIG. 5D) as well as the absence of diffraction peak in the XRD spectrum (FIG. 5E). The atomic ratio of Pd/Ru/Rh verified by EDS characterization is ~79.0/10.1/10.9, which is consistent with the result (~77.2/12.0/10.8) determined by ICP-OES (FIG. 5F). The EDS elemental mappings (FIG. 5G) and line scan (FIG. 5H) further corroborate the ternary alloy structure of synthesized a-PdRuRh NPs.

For comparison, monometallic amorphous Pd NPs (as referred to a-Pd NPs), and crystalline Pd and PdRu NPs with conventional fee phase, denoted as fcc-Pd and fcc-PdRu, respectively, were also prepared for catalytic performance comparison.

Preparation of Catalyst Slurry for Catalytic Ring-Opening Reaction of SO

An exemplary process of prepartion of catalyst slurry for catalytic ring-opening reaction of SO is described as follows. First, after 7 mg of Vulcan XC-72R carbon black were dispersed in 7 mL of ethanol in a vial, the as-obtained mixture was sonicated in an ice bath for 1 h to ensure the formation of the homogeneous suspension. Then, 3 mL of a catalyst solution, containing 3 mg of as-synthesized amorphous Pd-based NPs (e.g. a-PdRu NPs) (determined by ICP-OES), were dropwise added into the carbon suspension. The obtained mixture was then sonicated for another 1 h in an ice bath. After that, the catalyst loaded on carbon (catalyst/carbon) with an amorphous Pd-based NPs amount of 30 wt % was collected by centrifugation at 10,000 rpm for 10 min, followed by washing for six times with a mixture of chloroform (5 mL) and ethanol (5 mL). Subsequently, the catalyst/carbon was re-dispersed in 10 mL of ethanol for further usage.

Catalytic Ring-Opening Reaction of SO

All the catalytic ring-opening reactions of SO were conducted in the 25-mL Schlenk glass vessel tubes under $H_2$ (1 atm) atmosphere at room temperature (~25° C.). Specifically, 0.2 mmol of SO, 0.2 mmol of mesitylene used as an internal standard, and 1 mol % of catalyst/carbon (based on the ratio of noble metal/SO) were dispersed in 1 mL of ethanol under $H_2$ atmosphere. Composition of liquid samples taken during the ring-opening reaction were analyzed by GC-MS (Agilent 6890N GC system and Waters Quattro micro mass spectrometer with triple quadrupole detector) characterization. Samples of reaction at different reaction time were taken out and diluted with acetone, and then filtered by a filter membrane (with of pore size of 0.22 μm) to remove the catalysts. The samples were analyzed by GC-MS to monitor the conversion of SO and meanwhile to determine the selectivity of different products, including EPE and PE. Analysis times for products were typically on the order of 4.5-9.1 min depending upon the composition. Helium was used as the carrier gas at a constant flow rate of 1 mL/min. The column oven temperature was programmed from 70 to 200° C. at the rate of 20° C./min, and then raised to 280° C. at the rate of 30° C./min. The NMR (Bruker 500 MHz spectrometer) was used to analyze the formation of EPE product.

Catalytic Performance of the Ring-Opening Reaction of SO

Figure 6:
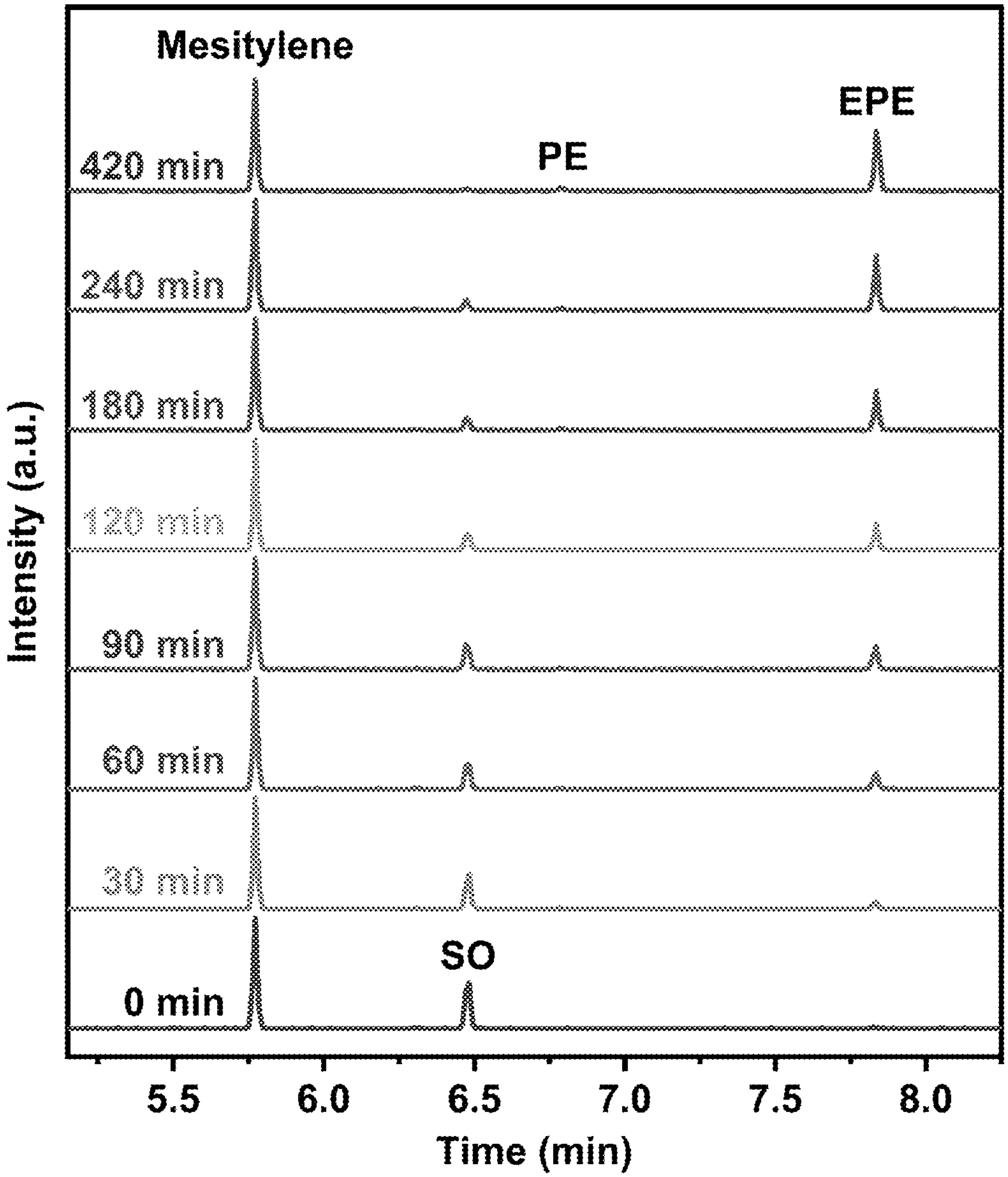
FIG. 6 is the gas chromatography-mass spectrometry (GC-MS) spectrum of ring-opening reaction of SO catalyzed by a-PdRu NPs.
Figure 7:
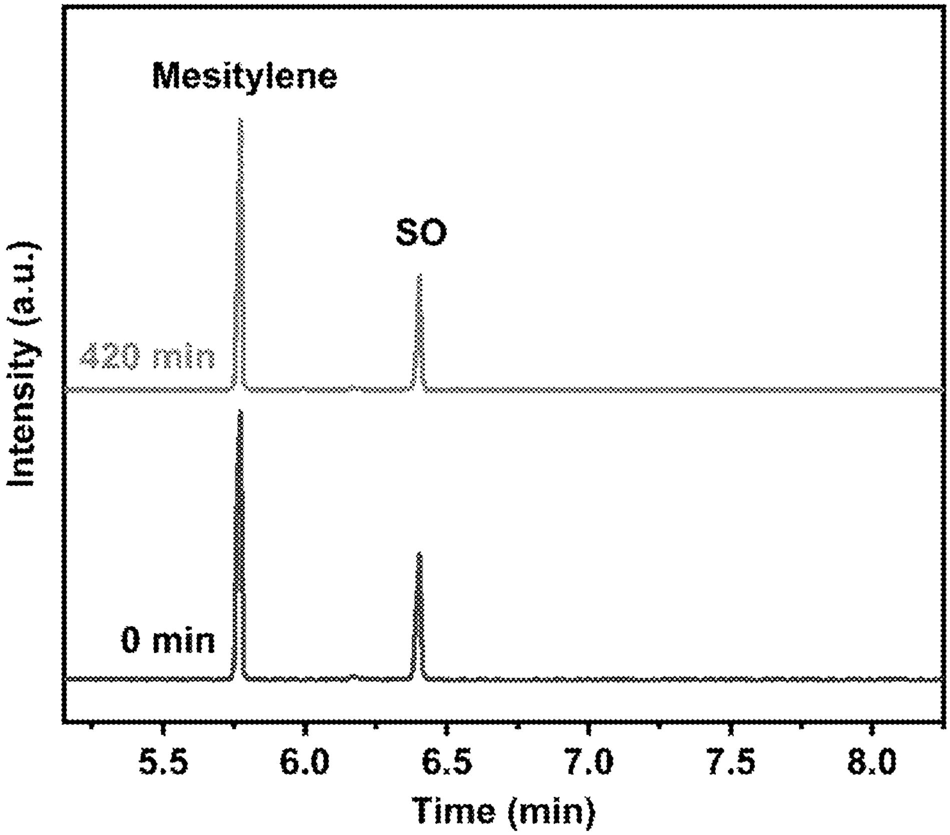
FIG. 7 is the GC-MS spectrum of ring-opening reaction of SO without any catalyst.

Referring to FIG. 6, the GC-MS spectra used for detecting the ring-opening reaction of SO catalyzed by a-PdRu NPs under $H_2$ atmosphere at room temperature shows that the ring-opening reaction of SO on the a-PdRu catalyst could be completed within 420 min. It can be seen that the ring-opening reaction of SO cannot occur without any catalyst since no product except the original SO was detected (FIG. 7).

Figure 8:
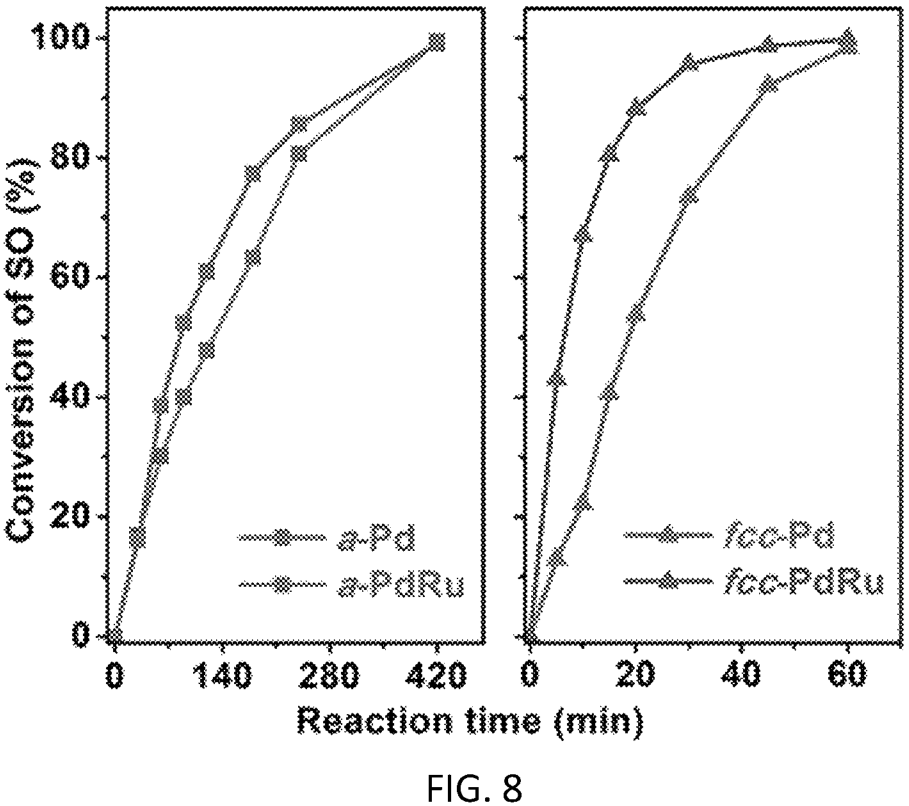
FIG. 8 are conversion rate curves of SO in the ring-opening reaction of a-Pd NPs, a-PdRu NPs, fcc-Pd NPs, and fcc-PdRu NPs.
Figure 9:
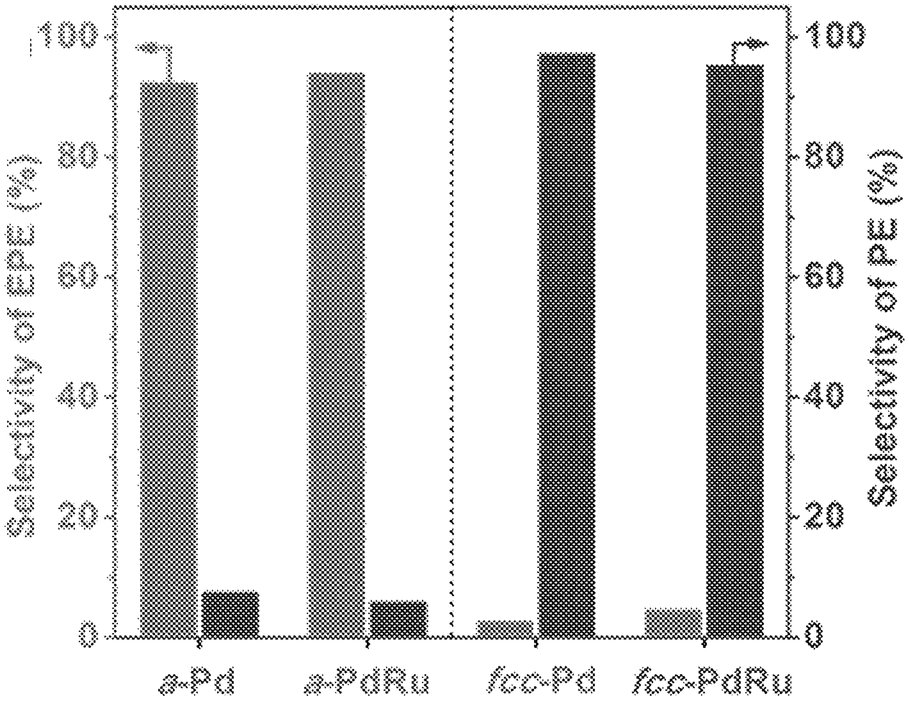
FIG. 9 are histograms of selectivity of EPE and PE products in ring-opening reaction of SO catalyzed by a-Pd NPs, a-PdRu NPs, fcc-Pd NPs, and fcc-PdRu NPs.
Figure 10:
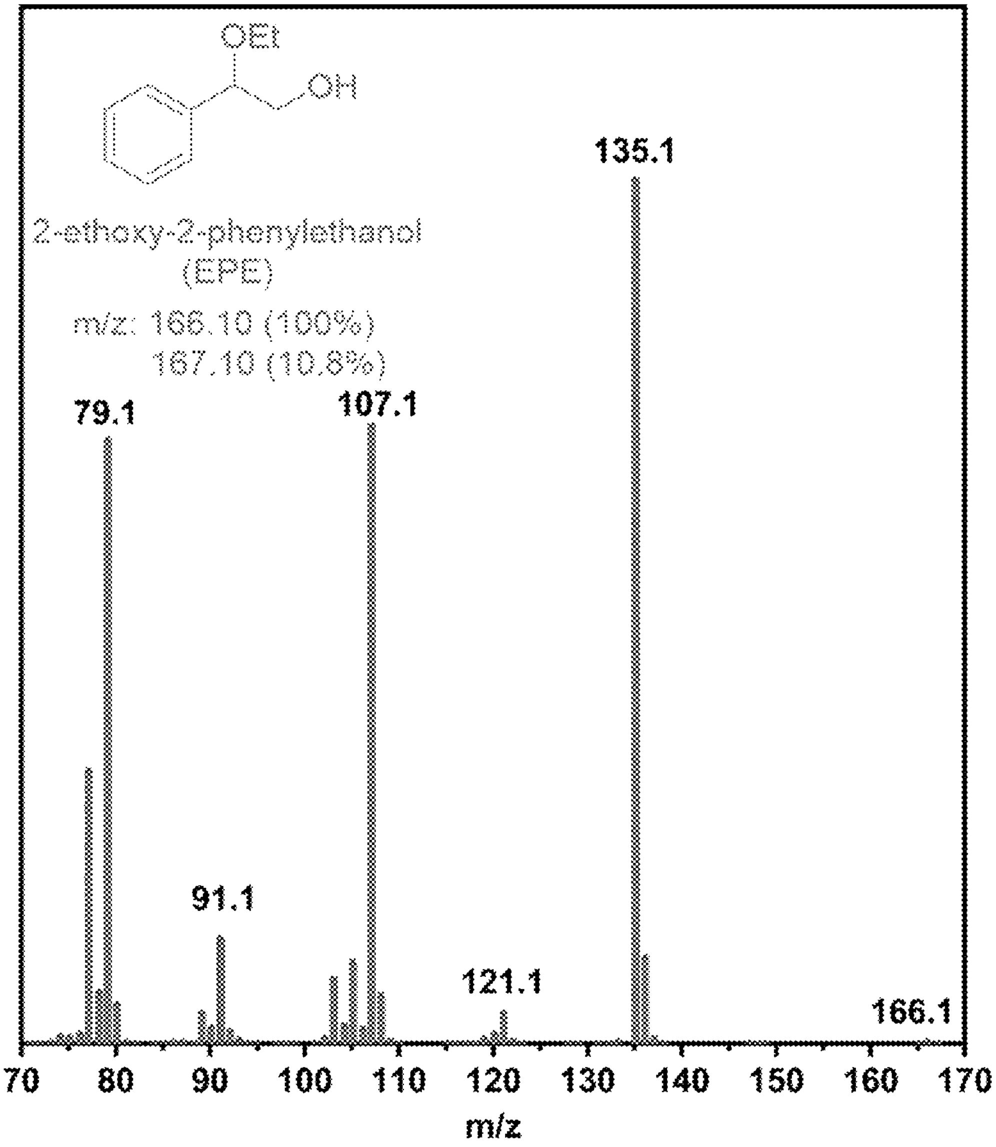
FIG. 10 is the total ion chromatogram (TIC) for detecting EPE (at ~7.85 min) in the ring-opening reaction of SO catalyzed by a-PdRu NPs.
Figure 11:
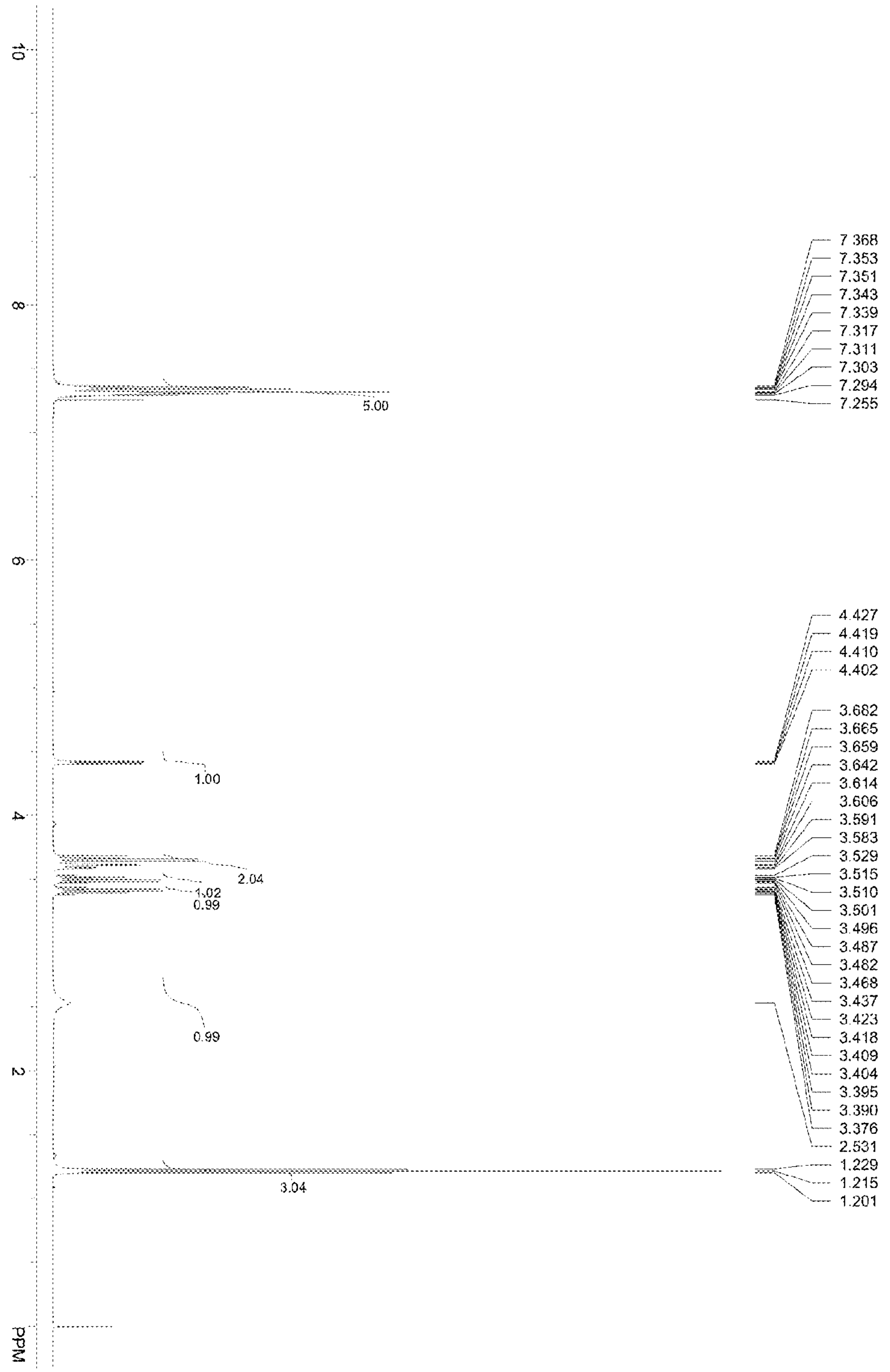
FIG. 11 is the $^1H$ nuclear magnetic resonance (NMR) spectrum of EPE.
Figure 12:
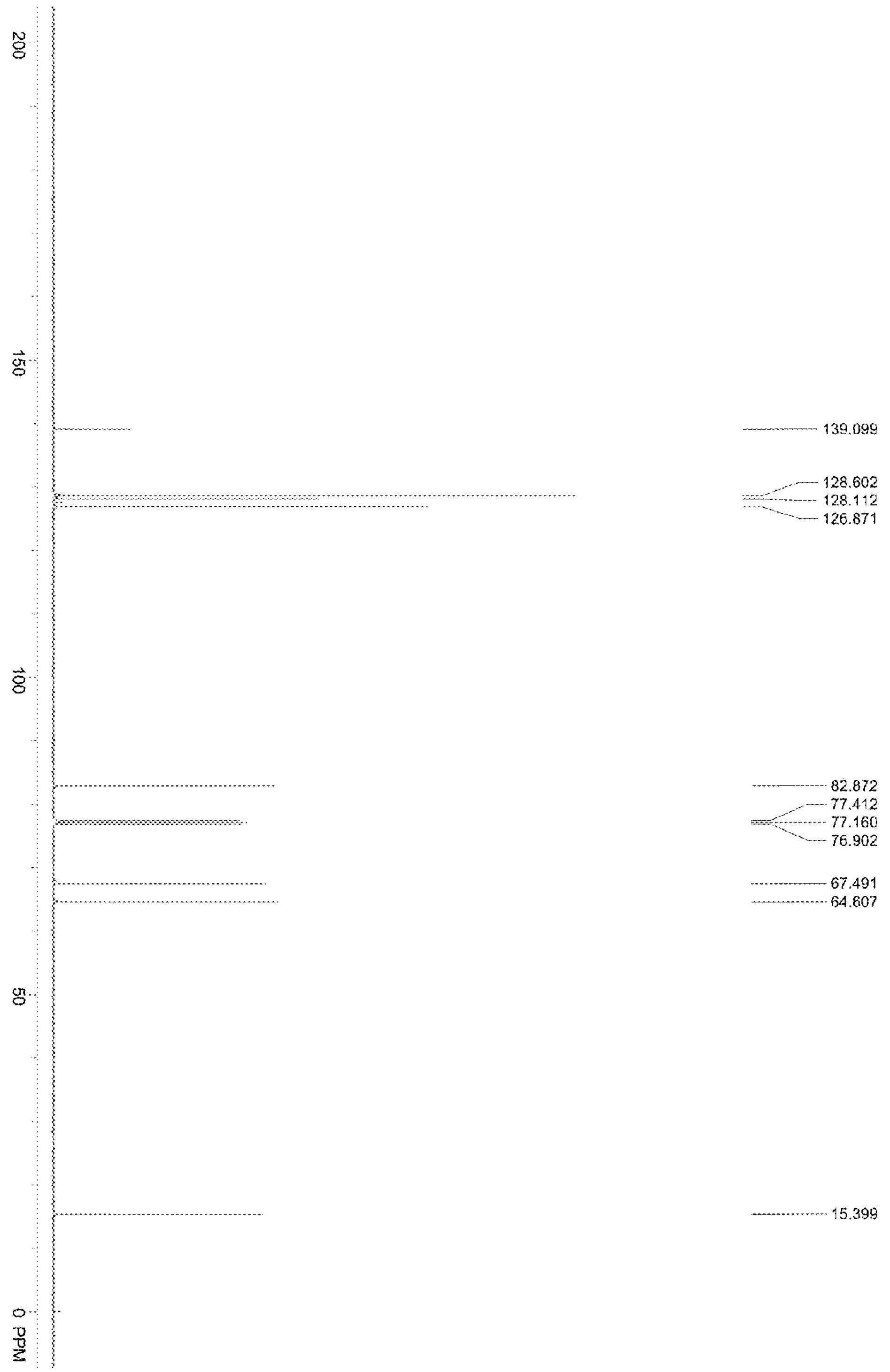
FIG. 12 is the $^{13}C$ NMR spectrum of EPE.

Referring to FIGS. 8 and 9, when the synthesized a-PdRu NPs are used as a catalyst, the alcoholysis reaction of SO occurs with a high SO conversion of >99% and the main product is EPE with a high selectivity of ~94% as analyzed by the GC-MS (FIG. 10) and the NMR spectra (FIGS. 11 and 12).

Figure 13A:
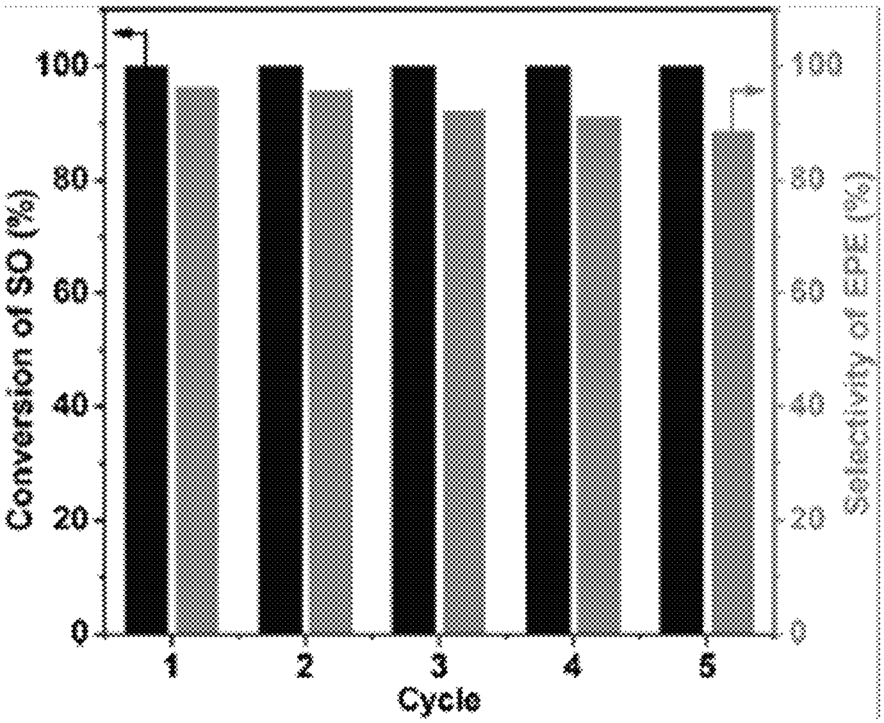
FIG. 13A illustrates conversion of SO and selectivity of EPE after using a-PdRu catalyst to catalyze the alcoholysis reaction of SO for 5 cycles.
Figure 13B:
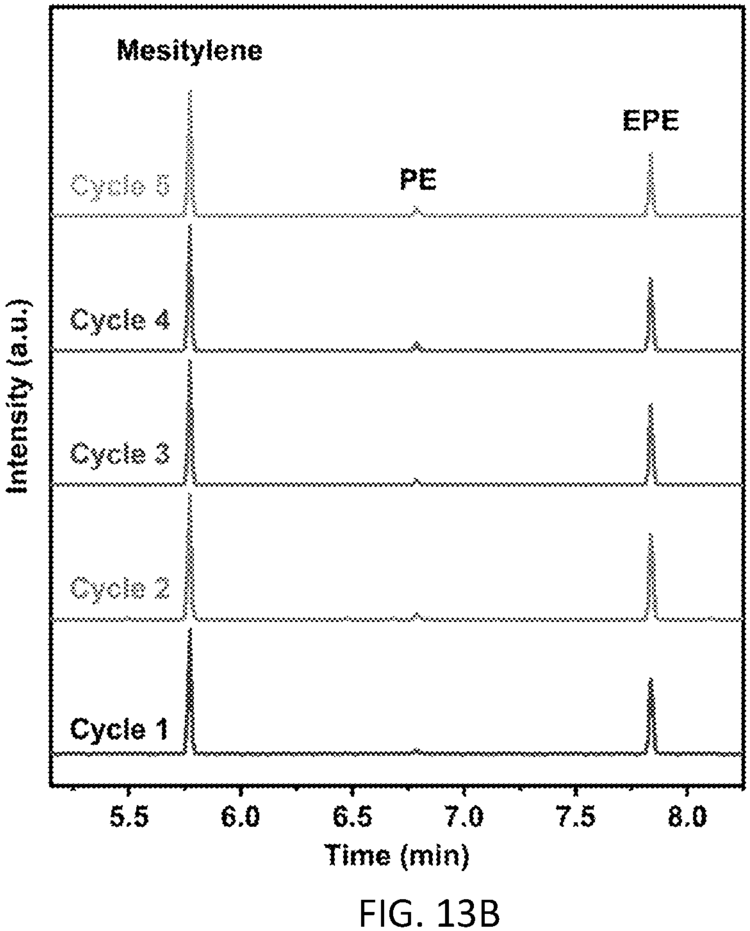
FIG. 13B illustrates the GC-MS spectrum of ring-opening reaction of SO catalyzed by the a-PdRu catalyst in different catalytic cycles.
Figure 13C:
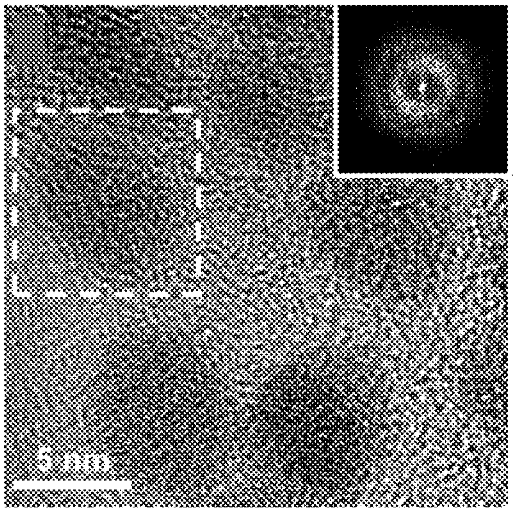
FIG. 13C illustrates the HRTEM image of a-PdRu catalyst after 5 catalytic cycles (Inset: the corresponding FFT pattern taken from the selected dashed square area).
Figure 13D:
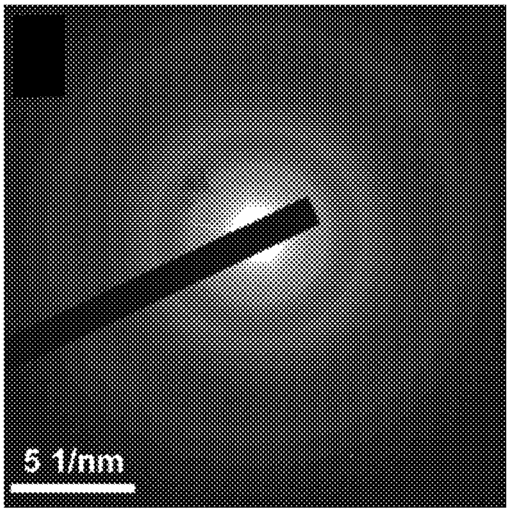
FIG. 13D illustrates the SAED pattern of a-PdRu catalyst after 5 catalytic cycles.

Furthermore, the recyclability of the a-PuRu catalyst towards the alcoholysis reaction of SO was studied. Referring to FIG. 13A, after 5 cycles of alcoholysis reaction, the conversion of SO and selectivity of EPE on the a-PdRu catalyst can be maintained as >99% and ~89%, respectively. In the GC-MS spectra (FIG. 13B) recorded during the recycling test, peaks appearing at ~5.77, 6.79, and 7.85 min correspond to mesitylene (used as an internal standard), PE, and EPE, respectively. After the recycling test, HRTEM image of the a-PdRu NPs (FIG. 13C) and the corresponding FFT pattern (Inset of FIG. 13C) verify that the disordered atomic arrangement can be maintained. The diffuse diffraction rings in the SAED pattern (FIG. 13D) further confirm that the a-PdRu NPs preserve their amorphous phase, indicating their good structural stability.

Figure 14:
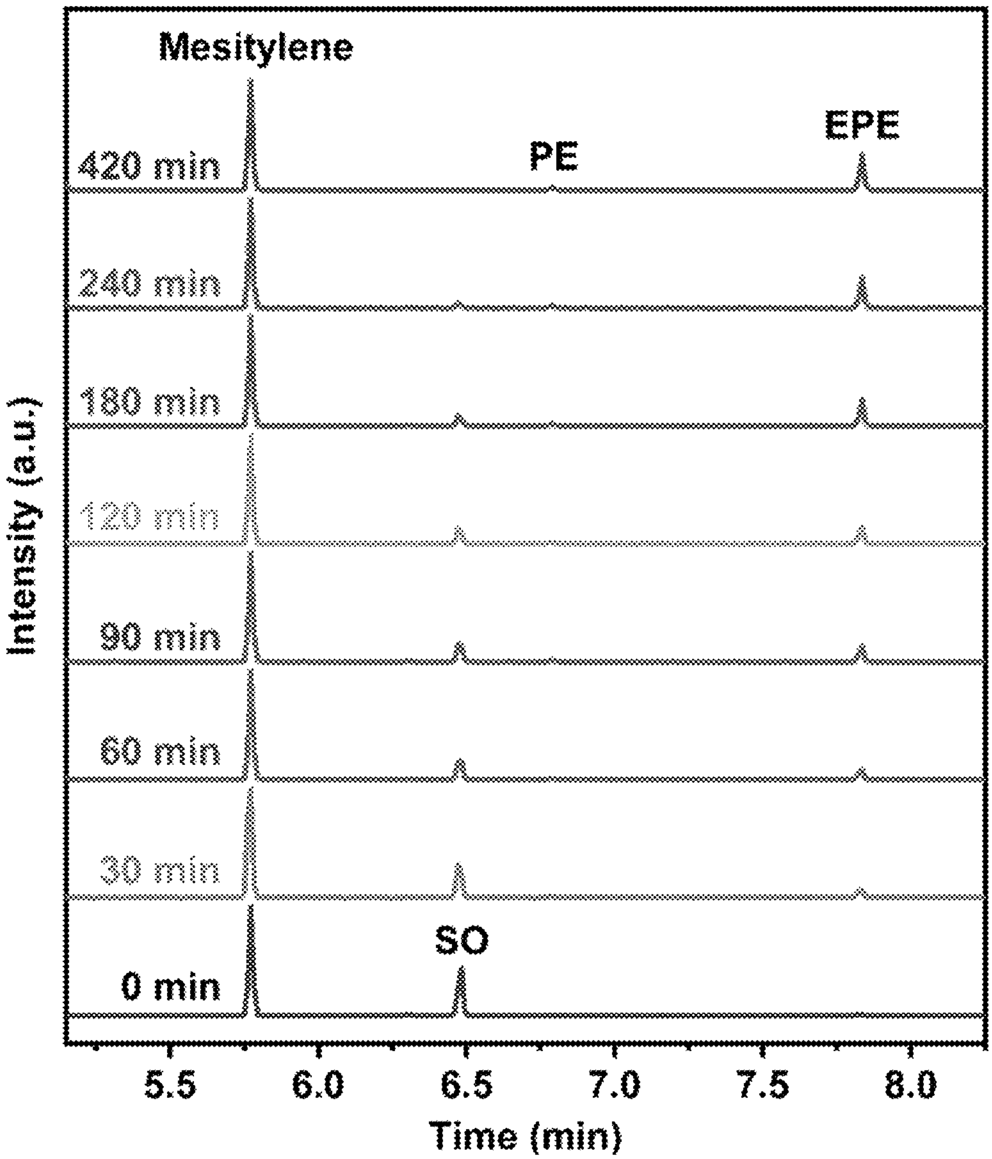
FIG. 14 illustrates GC-MS spectra of the ring-opening reaction of SO catalyzed by a-Pd NPs under $H_2$ atmosphere at room temperature.
Figure 15:
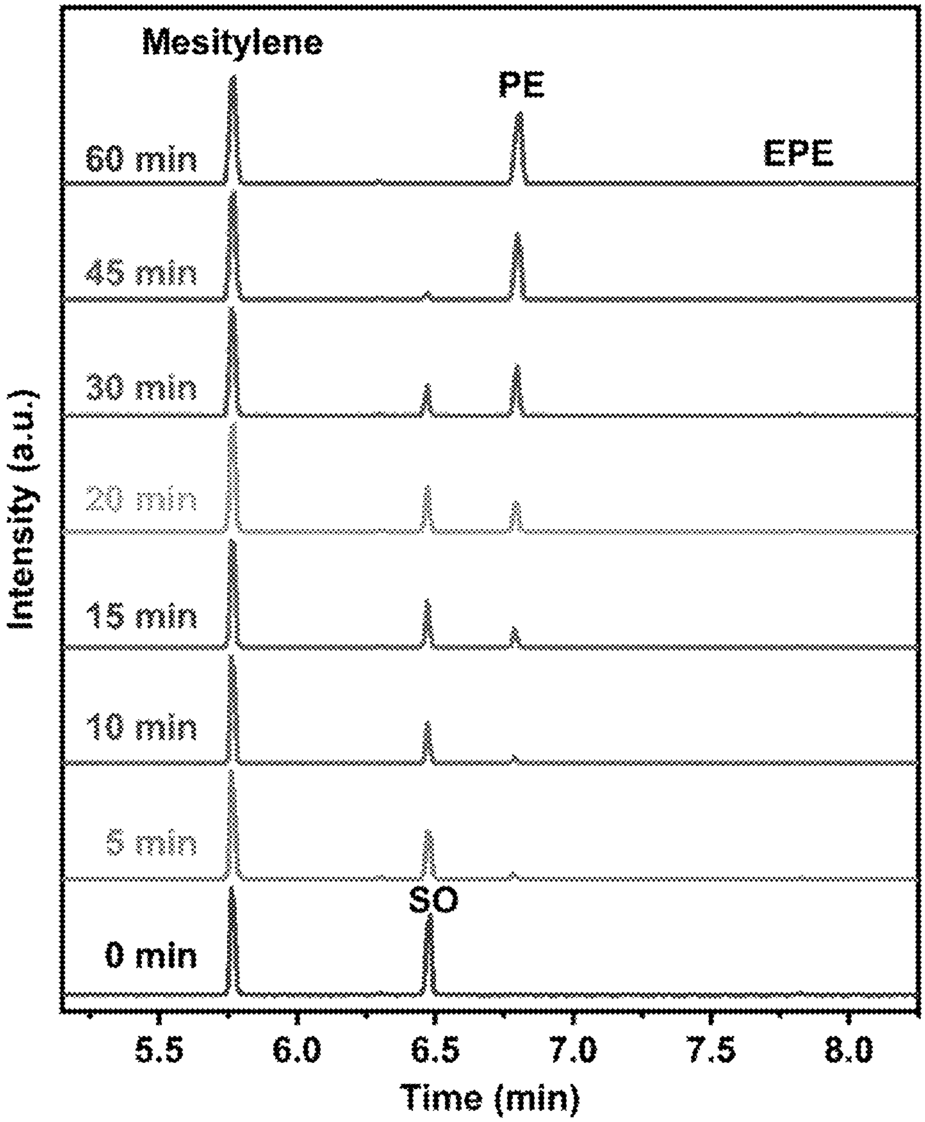
FIG. 15 illustrates GC-MS spectra of the ring-opening reaction of SO catalyzed by fcc-Pd NPs under $H_2$ atmosphere at room temperature.
Figure 16:
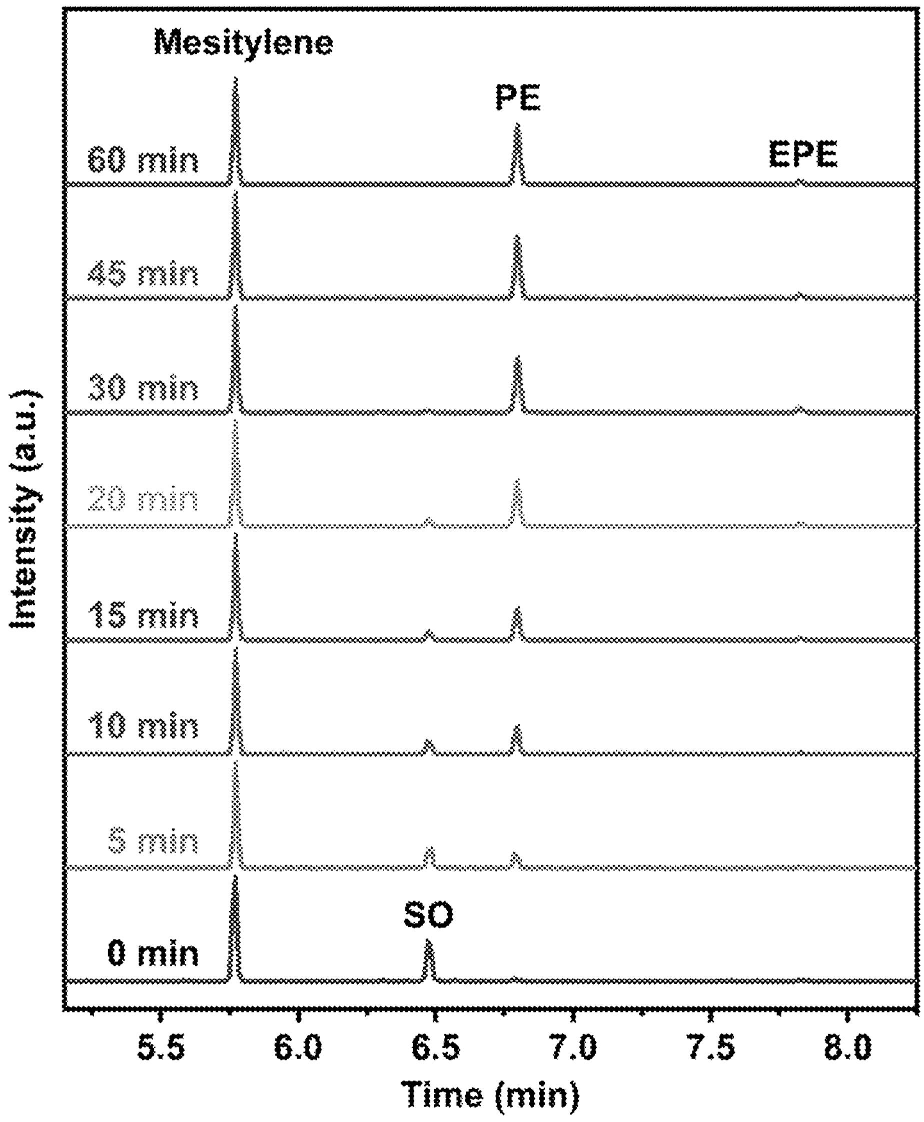
FIG. 16 illustrates GC-MS spectra of the ring-opening reaction of SO catalyzed by fcc-PdRu NPs under $H_2$ atmosphere at room temperature.

As shown in FIGS. 8, 9 and 14, compared to binary metallic a-Pd NPs the monometallic a-Pd NPs exhibit a slightly lower EPE selectivity of ~92% and slower conversion rate in the alcoholysis reaction of SO, which indicates that the alloying effect arising from the incorporation of Ru into Pd could boost the catalytic performance of the binary a-PdRu catalyst. As shown in Table 1, excellent catalytic performance of the amorphous Pd-based nanomaterials for the alcoholysis reaction of SO towards the production of EPE places them among the best of the state-of-art heterogeneous catalysts.

TABLE 1

Comparison of the catalytic performances of heterogeneous catalysts for the alcoholysis reaction of SO towards the synthesis of EPE

| Catalysts | Amount (/1 mmol SO) | Reaction temperature (° C.) | Conversion of SO (%) | Selectivity of EPE (%) |
|---|---|---|---|---|
| α-PdRu | 0.01 mmol (~1 mg) | r.t. (~25) | >99 | ~94 |
| α-Pd | 0.01 mmol (~1 mg) | r.t. (~25) | >99 | ~92 |
| $Ti_3C_2T_x$ MXenes | 1 mg | 60 | 99 | 50 |
| Gd-based MOF | 50 mg | 35 | 100 | 100 |
| La-based MOF | 41.8 mg | 70 | 77 | 100 |
| Fe-based MOF | 25 mg | 40 | N.A. | 35 |
| Functionalized MIL-101(Cr) MOF | 35 mg | r.t. | 84 | 100 |
| Sulfonic acid functionalized MOF | 0.02 mmol | r.t. | 94 | 99 |
| Lanthanide-organic coordination polymer | 50 mg | 35 | 99 | 100 |
| Graphite oxide | 1 mg | r.t. | N.A. | 72 |
| Polyoxometalate-modified rGO | 40 mg | r.t. | 96 | 90 |
| Acidic activated carbon | 100 mg | r.t. | N.A. | 84 |
| Acid treated carbon | 66.7 mg | r.t. | 99 | 97 |
| Nanoporous aluminosilicate | 50 mg | r.t. | 92 | 86 |
| Mesoporous aluminosilicate | 50 mg | r.t. | N.A. | 86 |
| Sulphated yttria-zirconia | 12 mg | 32 | N.A. | 96 |
| S, Fe-doped titanoniobate | 50 mg | r.t. | N.A. | 99 |
| $CuO/SiO_2$ | 125 mg | 60 | 99 | 90 |
| Pd/strontium hydroxyl fluoride | 12 mg | r.t. | 73 | 100 |
| $SiO_2$-supported Fe(III) catalyst | 22.2 mg | r.t. | N.A. | 100 |

Referring to FIGS. 8, 9, 15 and 16, the usage of crystalline fcc-Pd and fcc-PdRu NPs as catalysts would switch the ring-opening route of SO to a hydrogenation route, thus predominately forming PE product with high selectivity of ~97% and ~95%, respectively.

The aforementioned results unambiguously demonstrate that the phase structure of Pd-based nanocatalyst plays a significant role in controlling the ring-opening route of SO towards synthesis of different targeted products with high selectivity.

Preparation of Catalyst Slurry for Electrochemical HER

An exemplary process of preparation of catalyst slurry for electrochemical HER is described as follows. First, 540 μg of Vulcan XC-72R carbon black were dispersed in 540 μL of ethanol and the obtained mixture was sonicated in an ice bath for 1 h to make sure the formation of the homogeneous suspension. Then, 60 μL of catalyst solution, containing 60 μg of amorphous Pd-based NPs (e.g., a-PdRu NPs) (determined by ICP-OES), were dropwise added into the aforementioned carbon suspension, which was then sonicated for another 1 h in ice bath. After that, the as-obtained catalyst/carbon with amorphous Pd-based NPs amount of 10 wt % was collected by centrifugation at 14,800 rpm for 5 min, followed by washing six times with 1 mL of mixture solution composing of chloroform and ethanol (volume ratio of 1:1). After the catalyst/carbon was re-dispersed in a mixture solution containing 139 μL of isopropanol and 59 μL of water, 2 μL of Nafion™ solution were added and the mixed solution was sonicated for another 1 h in an ice bath to obtain the uniformly distributed catalyst slurry.

Electrochemical HER Measurements

The HER measurements were conducted on a CHI 760E electrochemical workstation at room temperature with the assistance of a glassy carbon electrode mounted on a rotator (glassy carbon rotating disk electrode (RDE)). A three-electrode system was used in the measurements. The glassy carbon RDE coated with catalyst, the graphite rod, and the Ag/AgCl (saturated KCl) electrode were employed as working electrode, counter electrode, and reference electrode, respectively. The Ag/AgCl electrode was calibrated with respect to a reversible hydrogen electrode (RHE)

Before drop-casting, the glassy carbon electrode (with diameter of 5 mm and area of 0.196 $cm^2$) is pre-polished with by $Al_2O_3$ slurry, then cleaned with deionized water and ethanol respectively. The working electrode was prepared by drop-casting 10 μL of the as-obtained catalyst slurry (containing 3.0 μg of amorphous Pd-based NPs) onto the glassy carbon electrode. The obtained electrode was dried under ambient conditions until the solvent was completely evaporated.

The phase-dependent catalysis of as-synthesized Pd-based nanomaterials toward electrochemical HER was investigated. Polarization curves were measured at room temperature with a scan rate of 5 mV $s^{-1}$ and a rotation rate of 1,600 revolutions per minute (rpm) in 0.5 M $H_2SO_4$ aqueous solution. EIS measurements were carried out in the frequency range of 0.1 Hz-100 kHz with 10 mV amplitude to obtain the solution resistance ($R_s$) and the charge transfer resistance ($K_{ct}$). All the polarization curves were corrected by $iR_s$ compensation.

For comparison, the HER measurements for the a-PdRh NPs, fcc-PdRh, a-Pd NPs, fcc-Pd NPs, and commercial Pt/C catalyst were conducted under the same conditions in 0.5 M $H_2SO_4$ aqueous solution.

Figure 17B:
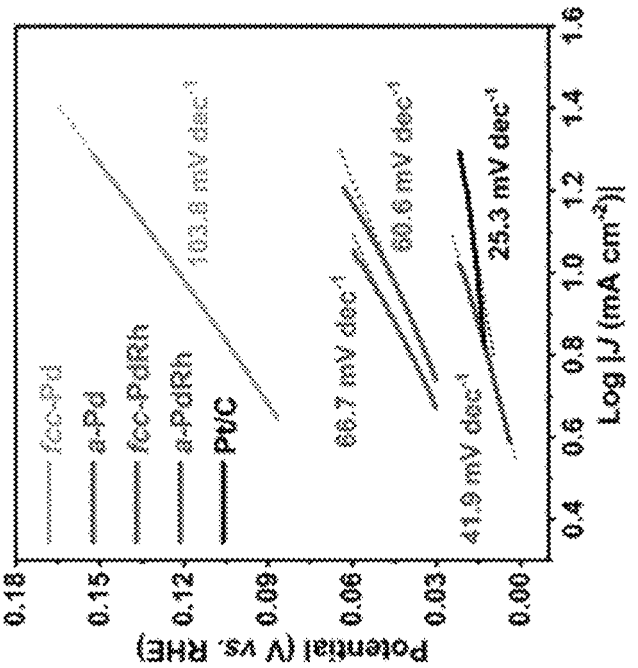
FIG. 17B illustrates the Tafel plots of a-Pd NPs, a-PdRh NPs, fcc-Pd NPs, fcc-PdRh NPs, and commercial Pt/C obtained from the corresponding polarization curves in FIG. 17A.
Figure 17A:
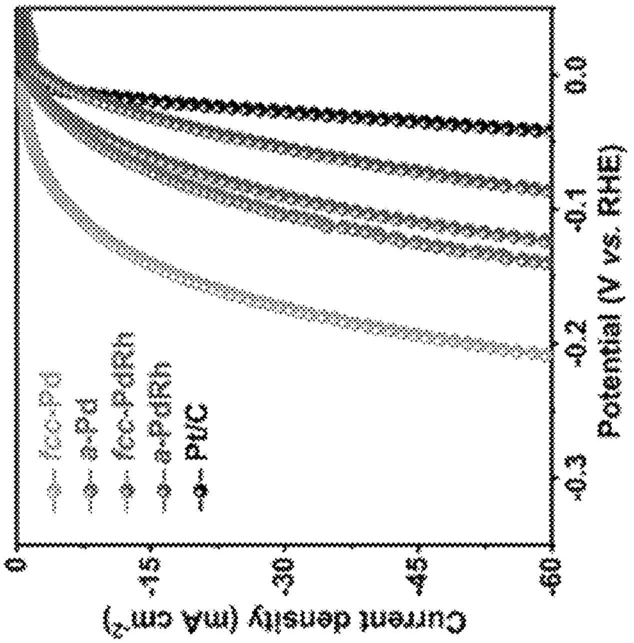
FIG. 17A illustrates the polarization curves of a-Pd NPs, a-PdRh NPs, fcc-Pd NPs, fcc-PdRh NPs and commercial Pt/C in electrocatalytic HER.

As demonstrated in the HER polarization curves in FIG. 17A, the a-PdRh and a-Pd catalysts exhibit significantly superior HER activities compared to their crystalline counterparts, i.e., fcc-PdRh and fcc-Pd, demonstrating the vital role of amorphous phase in boosting the HER performance. Moreover, when compared with the monometallic a-Pd and fcc-Pd NPs, the binary a-PdRh and fcc-PdRh catalysts show remarkably excellent HER activity, indicating that the incorporation of Rh into Pd could improve the HER catalytic performance. Referring to FIG. 17B, only a small overpotential of 20.6 mV is needed for the a-PdRh catalyst to achieve a current density of 10 mA $cm^{-2}$, which is comparable to that of commercial Pt/C (15.7 mV) and much lower than those of fcc-PdRh (46.8 mV), monometallic a-Pd (55.0 mV), and fcc-Pd (122.0 mV). Such low overpotential also places a-PdRh catalyst among the best of the reported Pd-based acidic HER electrocatalysts (Table 2).

Figure 17C:
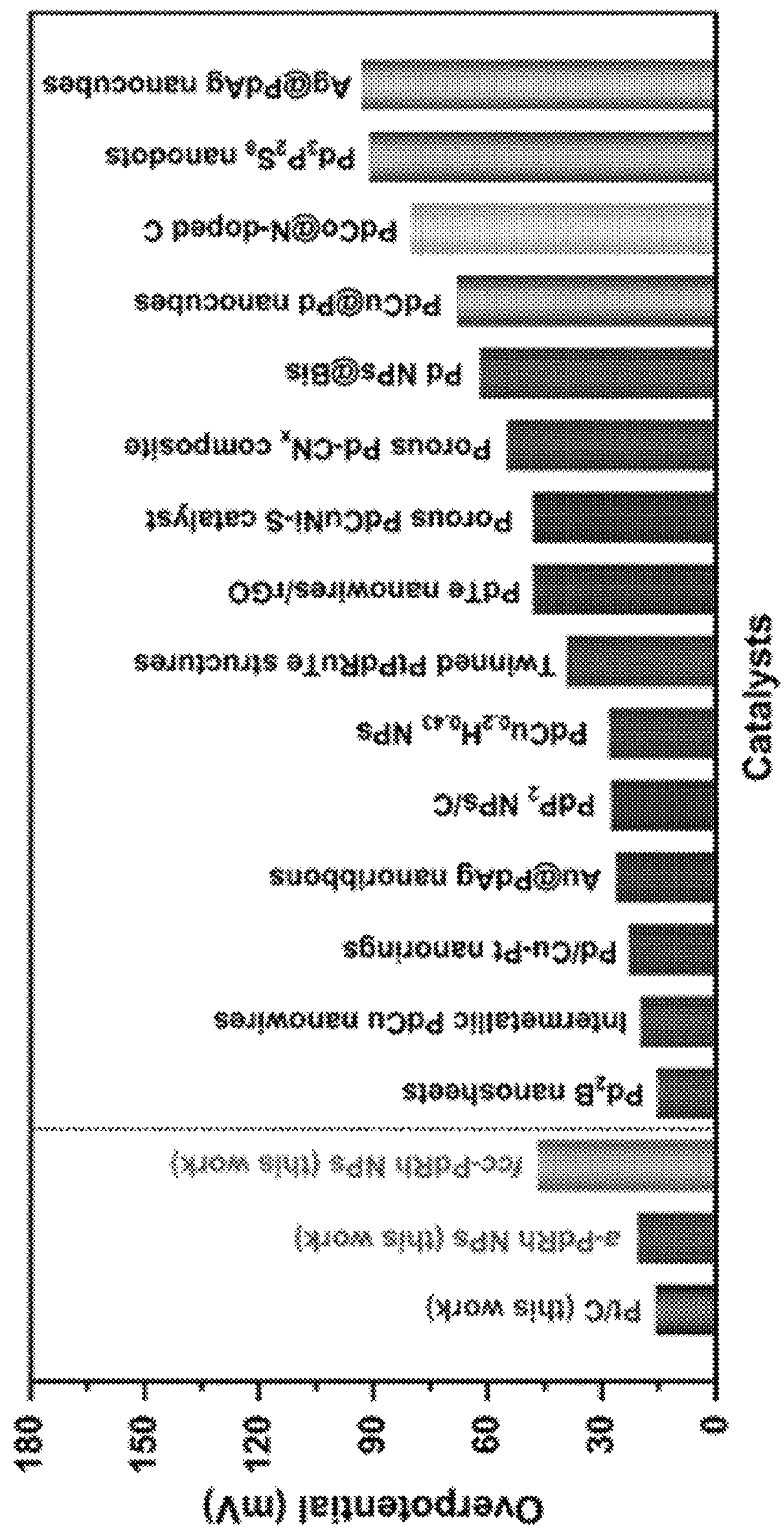
FIG. 17C illustrates the overpotentials at the current density of 10 mA $cm^{-2}$ for distinct catalysts and some previously reported Pd-based electrocatalysts (see Table 2 for more details).

Reaction kinetics distinct catalysts during the HER process can be evaluated by analyzing their Tafel slopes. As shown in FIG. 17C and Table 2, the Tafel slope of a-PdRh catalyst (41.9 mV $dec^{-1}$) is much lower than those of crystalline fcc-PdRh (60.6 mV $dec^{-1}$) and monometallic a-Pd (66.7 mV $dec^{-1}$), demonstrating the faster reaction kinetics of a-PdRh in HER.

TABLE 2

Summary of electrocatalytic HER performances of Pd-based catalysts in acidic media

| Catalyst | Electrolyte | Overpotential (mV) at 10 mA $cm^{-2}$ | Tafel slope (mV $dec^{-1}$) |
|---|---|---|---|
| α-PdRh NPs | 0.5M $H_2SO_4$ | 20.6 | 41.9 |
| fcc-PdRh NPs | 0.5M $H_2SO_4$ | 46.8 | 60.6 |
| α-Pd NPs | 0.5M $H_2SO_4$ | 55.0 | 66.7 |
| fcc-Pd NPs | 0.5M $H_2SO_4$ | 122.0 | 103.8 |
| Pt/C | 0.5M $H_2SO_4$ | 15.7 | 25.3 |
| $Pd_2B$ nanosheets | 0.5M $H_2SO_4$ | 15.3 | 22.5 |
| Intermetallic PdCu nanowires | 0.5M $H_2SO_4$ | 19.7 | 27 |
| Pd/Cu—Pt nanorings | 0.5M $H_2SO_4$ | 22.8 | 25 |
| Au@PdAg nanoribbons | 0.5M $H_2SO_4$ | 26.2 | 30 |
| $PdP_2$ NPs/C | 0.5M $H_2SO_4$ | 27.5 | 29.5 |
| $PdCu_{0.2}H_{0.43}$ NPs | 0.5M $H_2SO_4$ | 28 | 23 |
| Twinned PtPdRuTe structures | 0.5M $H_2SO_4$ | 39 | 32 |
| PdTe nanowires/rGO | 0.5M $H_2SO_4$ | 48 | 63 |
| Porous PdCuNi—S catalyst | 0.5M $H_2SO_4$ | 48 | 35 |
| Porous Pd—$CN_x$ composite | 0.5M $H_2SO_4$ | 55 | 35 |
| Pd NPs@Bis | 0.5M $H_2SO_4$ | 62 | 30 |
| PdCu@Pd nanocubes | 0.5M $H_2SO_4$ | 68 | 35 |
| PdCo@N-doped C | 0.5M $H_2SO_4$ | 80 | 31 |
| $Pd_3P_2S_8$ nanodots | 0.5M $H_2SO_4$ | 91 | 29 |
| Ag@PdAg nanocubes | 0.5M $H_2SO_4$ | 93 | 70 |
| Pd/Bi/Cu hierarchical structures | 0.5M $H_2SO_4$ | 79 | 61 |
| Pd NPs/$TiO_2$ nanospheres | 0.5M $H_2SO_4$ | 108 | 64 |

Figure 18A:
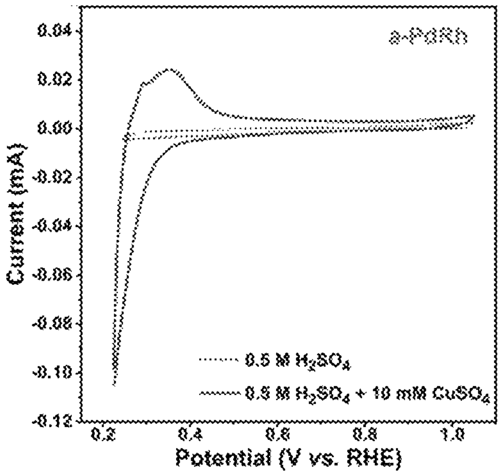
FIGS. 18A to 18C illustrate cyclic voltammetry (CV) curves of a-PdRh, fcc-PdRh and a-Pd catalysts measured at a scan rate of 10 mV $s^{-1}$ in $N_2$-saturated 0.5 M $H_2SO_4$ aqueous solution in the presence and absence of 10 mM CuSO4, respectively.
Figure 18B:
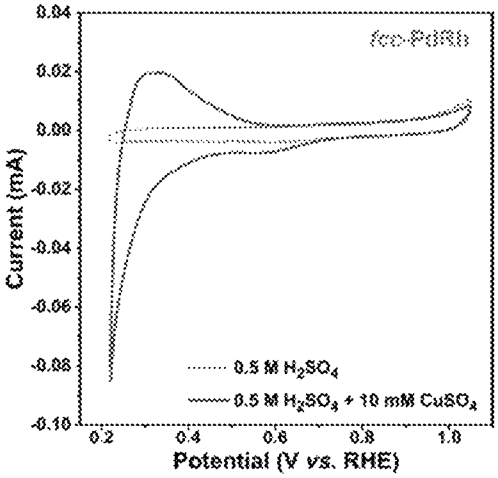
Figure 18C:
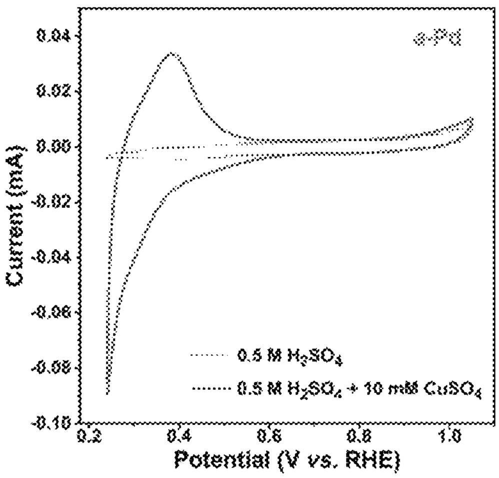

FIGS. 18A to 18C illustrates CV curves of a-PdRh, fcc-PdRh and a-Pd catalysts measured at a scan rate of 10 mV $s^{-1}$ in $N_2$-saturated 0.5 M $H_2SO_4$ aqueous solution in the presence and absence of 10 mM $CuSO_4$, respectively. In order to further investigate the intrinsic activities of these catalysts, the TOF values of a-PdRh, fcc-PdRh, and a-Pd catalysts were determined based on the numbers of active sites which were estimated through copper (Cu) underpotential deposition (UPD) method. In detail, the number of active sites (n) is calculated according to the Cu UPD stripping charge (Qcu) based on the following equation:

$$n=Q_{Cu}/(2Fm)$$

where F is the Faraday constant (96485 C $mol^{-1}$), m is the loading mass of noble metals ($3\times10^{-6}$ g in this work), and the constant 2 means two electrons transferred in the process of Cu UPD stripping ($Cu_{upd}\rightarrow Cu^{2+}+2e^-$).

Figure 19:
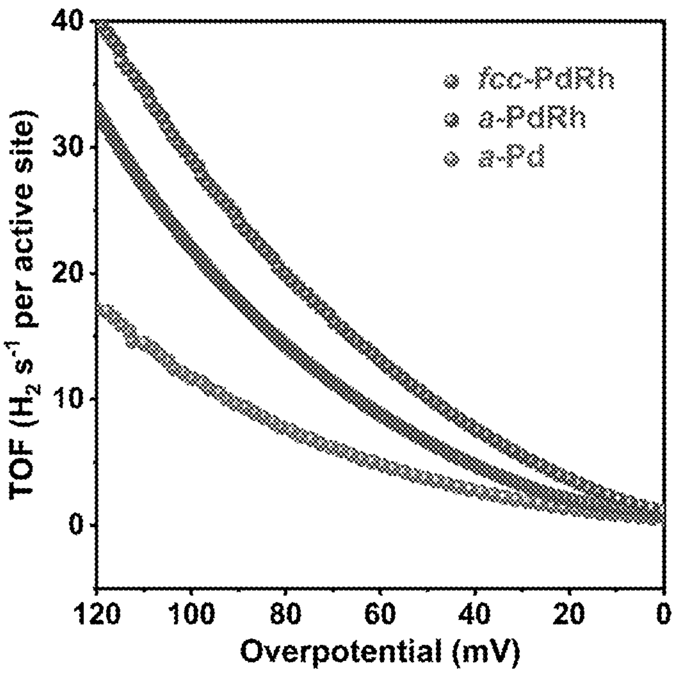
FIG. 19 shows TOF values of a-PdRh, fcc-PdRh, and a-Pd catalysts measured in 0.5 M $H_2SO_4$ aqueous solution.

FIG. 19 shows TOF values of a-PdRh, fcc-PdRh, and a-Pd catalysts measured in 0.5 M $H_2SO_4$ aqueous solution. The TOF value ($H_2$ $s^{-1}$) is calculated on the basis of the following equation: TOF=I/(2Fnm), where I is the current (A) during polarization curve test. The constant 2 indicates the number of electrons transferred in the HER process, as two electrons are required to form one $H_2$ molecule.

As shown in FIG. 19, the a-PdRh catalyst exhibits remarkably higher TOF values compared with those of crystalline fcc-PdRh and monometallic a-Pd. Specifically, at the overpotentials of 25, 50, 75, and 100 mV, the TOF values of a-PdRh catalyst are 4.6, 10.2, 18.1, and 29.3 $H_2$ $s^{-1}$, respectively, surpassing many reported metal-based electrocatalysts in the same electrolyte (Table 3), which verifies the excellent HER activity of the as-synthesized a-PdRh catalyst in acidic media.

TABLE 3

Comparison of the TOF values of α-PdRh catalyst with some reported metal-based electrocatalysts toward HER in acidic media.

| Catalyst | Electrolyte | Overpotential (mV) | TOF ($H_2$ $s^{-1}$) |
|---|---|---|---|
| α-PdRh | 0.5M $H_2SO_4$ | 25 | 4.6 |
| | | 50 | 10.2 |
| | | 75 | 18.1 |
| | | 100 | 29.3 |
| Ir NPs/hollow carbon | 0.5M $H_2SO_4$ | 25 | 4.21 |
| Ru on nitrogenated carbon | 0.5M $H_2SO_4$ | 25 | 0.67 |
| $PdP_2$ NPs/C | 0.5M $H_2SO_4$ | 27.5 | 0.32 |
| Nanoporous Ag@Pd—Pt | 0.5M $H_2SO_4$ | 75 | 3.26 |
| Pd NPs@Bis | 0.5M $H_2SO_4$ | 80 | 2.33 |

TABLE 3-continued

Comparison of the TOF values of α-PdRh catalyst with some reported metal-based electrocatalysts toward HER in acidic media.

| Catalyst | Electrolyte | Overpotential (mV) | TOF ($H_2\ s^{-1}$) |
|---|---|---|---|
| $PdCu_{0.2}H_{0.43}$ NPs | 0.5M $H_2SO_4$ | 100 | 1.34 |
| Porous PdCuNi—S catalyst | 0.5M $H_2SO_4$ | 100 | 0.032 |
| W—Mo dual-atom catalyst | 0.5M $H_2SO_4$ | 100 | 2.36 |
| Pt single atoms on graphene | 0.5M $H_2SO_4$ | 100 | 26.41 |
| $Pd_3P_2S_8$ nanodots | 0.5M $H_2SO_4$ | 140 | 1.6 |
| Pt clusters/MXene | 0.5M $H_2SO_4$ | 200 | 10.66 |

Figure 20A:
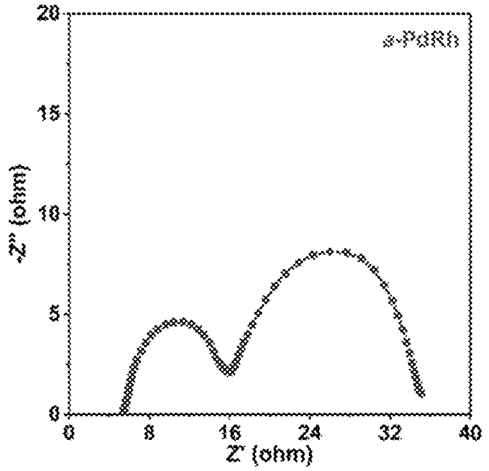
FIGS. 20A to 20C illustrate the electrochemical impedance spectroscopy (EIS) measurement results of a-PdRh, fcc-PdRh, and a-Pd catalysts, respectively.
Figure 20B:
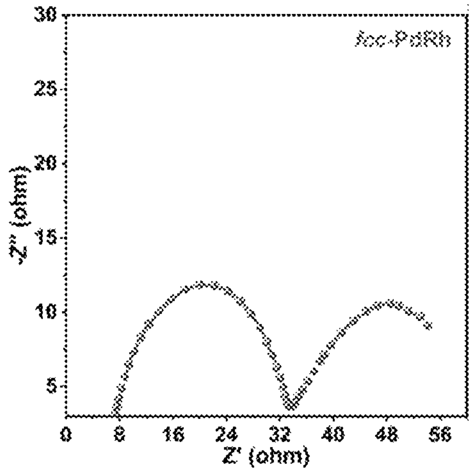
Figure 20C:
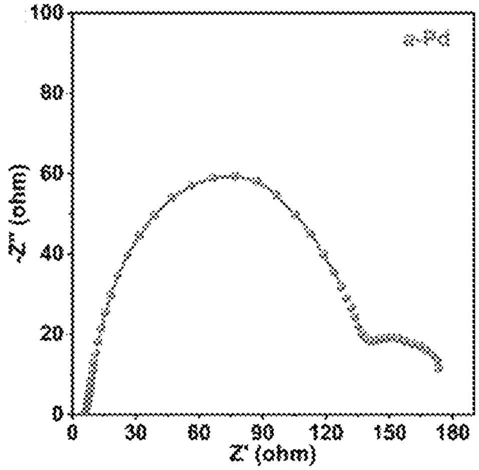

Furthermore, the EIS measurement results of a-PdRh, fcc-PdRh, and a-Pd catalysts (FIGS. 20A to 20C) unravel that the a-PdRh catalyst obviously possesses a smaller charge transfer resistance compared to the crystalline fcc-PdRh and monometallic a-Pd, affirming the fast charge transfer and favorable HER kinetics on a-PdRh. The aforementioned results demonstrate that the amorphous phase and the doping of Rh into Pd both contribute to the superior HER performance of the synthesized a-PdRh catalyst.

The embodiments may be chosen and described in order to best explain the principles of the invention and its practical application, thereby enabling others skilled in the art to understand the invention for various embodiments and with various modifications that are suited to the particular use contemplated. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations. While the apparatuses disclosed herein have been described with reference to particular structures, shapes, materials, composition of matter and relationships . . . etc., these descriptions and illustrations are not limiting. Modifications may be made to adapt a particular situation to the objective, spirit and scope of the present disclosure. All such modifications are intended to be within the scope of the claims appended hereto.

What is claimed is:

1. A method for synthesizing amorphous Pd-based metallic alloy nanoparticles, comprising:

a) dissolving Pd(ID) acetate as a Pd precursor in a first solvent to form a first solution;

b) mixing the first solution with a second solvent to form a first mixture;

c) adding surfactant into the first mixture to form a second mixture;

d) heating the second mixture at a first heating temperature for a first heating time to render a second solution;

e) adding a metal precursor into the second solution to form a third mixture;

f) heating the third mixture at a second heating temperature for a second heating time to render a third solution;

g) naturally cooling down the third solution to a room temperature;

h) adding ethanol to the third solution to form a fourth solution; and i) collecting the amorphous Pd-based metallic alloy nanoparticles from the fourth solution by centrifugation; and wherein the metal precursor is a Ru precursor, a Rh precursor or a combination thereof.

2. The method of claim 1, wherein the Pd precursor has a purity of greater than or equal to 98%; the first solvent is a toluene having a purity of greater than or equal to 99.5%; and a concentration of Pd precursor to the toluene is in a range from 1 to 20 mg/ml.

3. The method of claim 1, wherein the second solvent is an oleylamine having a purity greater than or equal to 70%; and a volume ratio of the oleylamine to the first solution is in a range from 20:1 to 3:1.

4. The method of claim 1, wherein the surfactant is 1-propanethiol, 1-octanethiol, 2-ethylhexanethiol, 1-dodecanethiol, 1-tetradecanethiol, 1-hexadecanethiol, 1-octadecanethiol, triphenylphosphine, trioctylphosphine, or combinations thereof.

5. The method of claim 1, wherein the first heating temperature is in a range from 140° C. to 200° C.; and the first heating time is in a range from 15 to 25 minutes.

6. The method of claim 1, wherein the metal precursor has a purity greater than or equal to 99.98%; and a molar ratio of the metal precursor to the Pd precursor is in a range from 1:10 to 5:1.

7. The method of claim 1, wherein the second heating temperature is in a range from 140° C. to 200° C.; and the second heating time is in a range from 45 to 75 minutes.

8. The method of claim 1, wherein a volume ratio of the ethanol to the third solution is in a range from 1:1 to 5:1.

9. The method of claim 2, wherein the concentration of Pd precursor to the toluene is 10 mg/ml.

10. The method of claim 3, wherein the surfactant is a $C_3$-$C_{20}$ alkanethiol, an organophosphorus compound or the combination thereof.

11. The method of claim 4, wherein the surfactant has a purity greater than or equal to 98%; and a molar ratio of the surfactant to Pd precursor is in a range from 1:2 to 2:1.

12. The method of claim 11, wherein the molar ratio of the surfactant to Pd precursor is 1:1.

13. The method of claim 5, wherein the first heating temperature is 155° C.; and the first heating time is 20 minutes.

14. The method of claim 6, wherein the molar ratio of the metal precursor to the Pd precursor is 1:2.

15. The method of claim 14, wherein the step e) further comprising dissolving the metal precursor in a solvent before adding the metal precursor into the second solution.

16. The method of claim 7, wherein the second heating temperature is 155° C.; and the second heating time is 60 minutes.

17. A method of preparing a catalyst, comprising:

synthesizing amorphous Pd-based metallic alloy nanoparticles with the method of claim 1:

dispersing carbon powder in ethanol to obtain a fourth mixture;

sonicating the fourth mixture in an ice bath for one hour to form a carbon suspension;

adding the synthesized amorphous Pd-based metallic alloy nanoparticles into the carbon suspension to obtain a fifth mixture;

sonicating the fifth mixture in an ice bath for one hour to form a catalyst-loaded carbon suspension;

collecting the catalyst-loaded carbon from the suspension by centrifugation;

washing the catalyst-loaded carbon with a mixture solution composing of chloroform and ethanol;

re-dispersing the catalyst-loaded carbon in a mixture solution containing isopropanol and water to form a sixth mixture;

adding sulfonated tetrafluoroethylene based fluoropolymer-copolymer dispersion into the sixth mixture to form a seventh mixture; and sonicating the seventh mixture in an ice bath for one hour to form a catalyst.

18. A method of performing an epoxide ring-opening reaction or an electrochemical hydrogen evolution reaction utilizing the catalyst prepared with the method of claim 17.

* * * * *